United States Patent
Soto Jara et al.

(10) Patent No.: US 12,265,089 B2
(45) Date of Patent: *Apr. 1, 2025

(54) DISCRIMINATING PARKINSON'S DISEASE FROM MULTIPLE SYSTEM ATROPHY USING ALPHA-SYNUCLEIN PMCA

(71) Applicants: Board of Regents of the University of Texas System, Austin, TX (US); Amprion, Inc., San Francisco, CA (US)

(72) Inventors: Claudio Soto Jara, Friendswood, TX (US); Mohammad Shahnawaz, Houston, TX (US); Luis Concha, San Diego, CA (US)

(73) Assignees: Board of Regents of the University of Texas System, Austin, TX (US); Amprion, Inc., San Francisco, CA (US)

( * ) Notice: Subject to any disclaimer, the term of this patent is extended or adjusted under 35 U.S.C. 154(b) by 1029 days.

This patent is subject to a terminal disclaimer.

(21) Appl. No.: 17/154,966

(22) Filed: Jan. 21, 2021

(65) Prior Publication Data

US 2021/0164998 A1    Jun. 3, 2021

Related U.S. Application Data

(63) Continuation-in-part of application No. 17/011,374, filed on Sep. 3, 2020, now Pat. No. 11,079,396, and a continuation-in-part of application No. 14/852,475, filed on Sep. 11, 2015, now Pat. No. 10,989,718.

(60) Provisional application No. 63/073,420, filed on Sep. 1, 2020, provisional application No. 63/073,424, filed on Sep. 1, 2020, provisional application No. 63/045,593, filed on Jun. 29, 2020, provisional application No. 63/042,679, filed on Jun. 23, 2020, provisional application No. 63/040,144, filed on Jun. 17, 2020, provisional application No. 62/963,805, filed on Jan. 21, 2020, provisional application No. 62/895,535, filed on Sep. 4, 2019, provisional application No. 62/049,304, filed on Sep. 11, 2014.

(51) Int. Cl.
| | | |
|---|---|---|
| *G01N 33/68* | (2006.01) | |
| *A61B 8/13* | (2006.01) | |
| *G01N 33/58* | (2006.01) | |

(52) U.S. Cl.
CPC .......... *G01N 33/6893* (2013.01); *A61B 8/13* (2013.01); *G01N 33/582* (2013.01); *G01N 2800/2835* (2013.01); *G01N 2800/2878* (2013.01)

(58) Field of Classification Search
CPC ............ G01N 33/6893; G01N 33/582; G01N 2800/2835; G01N 2800/2878; G01N 33/6896; G01N 2800/2814
See application file for complete search history.

(56) References Cited

U.S. PATENT DOCUMENTS

| 10,989,718 B2 * | 4/2021 | Jara .................. G01N 33/6896 |
| 11,079,396 B2 * | 8/2021 | Concha ............. G01N 33/6896 |
| 11,959,927 B2 * | 4/2024 | Concha ............. G01N 33/6896 |
| 2005/0176078 A1 | 8/2005 | Allsop |
| 2008/0118938 A1 | 5/2008 | Estrada |
| 2011/0111014 A1 | 5/2011 | Langston |
| 2012/0094307 A1 | 4/2012 | Tajima |
| 2013/0137112 A1 | 5/2013 | Patton et al. |
| 2016/0077111 A1 | 3/2016 | Jara et al. |
| 2017/0166955 A1 | 6/2017 | Birnboim et al. |
| 2019/0302128 A1 | 10/2019 | Green et al. |
| 2020/0232996 A1 | 7/2020 | Caughey et al. |

FOREIGN PATENT DOCUMENTS

| WO | 2008030973 |  | 3/2008 |
| WO | 2012099884 |  | 7/2012 |
| WO | 2018007817 | A1 | 1/2018 |
| WO | 2018170324 |  | 9/2018 |
| WO | 2019203645 |  | 10/2019 |

OTHER PUBLICATIONS

Jordi Pujols, et al., "High-throughput Screening Methodology to Identify Alpha-Synuclein Aggregation Inhibitors", International Journal of Molecular Sciences, vol. 18, No. 3, Mar. 2, 2017 (Mar. 2, 2017), p. 478, XP0556568905, DOI: 10.3390/ijms18030478.

Mollenhauer B, et al., "Direct quantification of CSF alpha-synuclein by ELISA and first cross-sectional study in patients with neurodegeneration", Experimental Neurology, Elsevier, Amsterdam, NL, vol. 213, No. 2, Oct. 1, 2008 (Oct. 1, 2008), pp. 315-325, XP025426427, ISSN: 0014-4886, DOI: 10.1016/J.EXPNEUROL.2008.06.004 (retrieved on Jun. 14, 2008).

Published Japanese Translation No. 2005-528588 of the PCT International Application Japanese Patent Application Laid-Open No. 2010-043865.

2nd Office Action issued in Israeli Patent Application No. 251052, dated Sep. 18, 2021.

(Continued)

*Primary Examiner* — Olga N Chernyshev
(74) *Attorney, Agent, or Firm* — Benesch Friedlander Coplan & Aronoff LLP

(57) ABSTRACT

A method is provided for distinguishing between and/or diagnosing Parkinson's disease (PD) or multiple system atrophy (MSA) in a subject who is exhibiting symptoms associated with both PD and MSA. The method comprises: (A) contacting a biological sample obtained from the subject and comprising soluble, misfolded alpha-synuclein (αS) protein with a pre-incubation mixture comprising a monomeric αS substrate and an indicator to form an incubation mixture; (B) conducting an incubation cycle two or more times on the incubation mixture to form misfolded αS aggregates; (C) subjecting the incubation mixture to excitation and detecting via indicator fluorescence emission the misfolded αS aggregates; and (D) diagnosing the subject has having PD or MSA depending on the fluorescence emission intensity. In some aspects, the incubation cycles are conducted in the presence of a bead.

43 Claims, 18 Drawing Sheets

Specification includes a Sequence Listing.

(56) References Cited

OTHER PUBLICATIONS

1st Office Action issued in Israeli Patent Application No. 251052, dated Jul. 12, 2020.
Examination Report No. 1 issued in Australian Patent Application No. 2015314783, dated Dec. 17, 2020.
Preliminary Office Action issued in Brazilian Patent Application No. BR 11 2017 004899 0, dated Jun. 19, 2020.
Notice of Requisition issued in Canadian Patent Application No. 2,960,830, dated May 9, 2022.
Notice of Requisition issued in Canadian Patent Application No. 2,960,830, dated Jul. 9, 2021.
Notice of Requisition issued in Canadian Patent Application No. 2,960,830, dated Aug. 5, 2020.
First Office Action issued in Chinese Patent Application No. 2015800586063, dated Sep. 27, 2020.
Second Office Action issued in Chinese Patent Application No. 2015800586063, dated May 27, 2021.
Third Office Action issued in Chinese Patent Application No. 2015800586063, dated Nov. 22, 2021.
Rejection Decision issued in Chinese Patent Application No. 2015800586063, dated Mar. 3, 2022.
Notice of Reasons for Rejection issued in Japanese Patent Application No. 2017-533721, dated May 19, 2020.
Notice of Office Action issued in Korean Patent Application No. 10 2017 7009707, dated Sep. 24, 2021.
Notice to Submit Response issued in Korean Patent Application 10 2017 7009707, dated Mar. 28, 2022.
Office Action issued in Mexican Patent Application No. MX/a/2017/003269, dated Nov. 1, 2021.
Office Action issued in Mexican Patent Application No. MX/a/2017/003269, dated Apr. 1, 2022.
Examination Report issued in Indian Patent Application No. 201727012898, dated Mar. 3, 2021.
Exam Report issued in European Patent Application No. 15 839 278.7, dated Aug. 7, 2021.
Written Opinion issued in Singaporean Patent Application No. 10202008464U, dated Oct. 28, 2021.
Search Report issued in Singaporean Patent Application No. 10202008464U, dated Oct. 28, 2021.
Roostaee A. et al., Aggregation and neurotoxicity of recombinant α-synuclein aggregates initiated by dimerization. Mol Neurodegener, Jan. 22, 2013, vol. 8, No. 5, pp. 1-12. AbstractSection "protein misfolding cyclic amplification (PMCA) of a-Syn".
Westphal et al., Monomeric Synucleins Generate Membrane Curvature, The Journal of Biological Chemistry, Jan. 18, 2013, vol. 288, No. 3, pp. 18290-1840, Especially p. 1830 col 2 para 5, p. 1834 col 2 para 2, Abstract.
Fauerbach et al., Supramolecular Non-Amyloid Intermediates in the Early Stages of a-Synuclein Aggregation, Biophysical Journal, Mar. 7, 2012, vol. 102, No. 5, pp. 1127-1136, Especially p. 1128 col 1 para 3, p. 1132 col 2 para 2, Figure 3, Figure 4, Abstract.
International Search Report and Written Opinion mailed December 1420, for Application No. PCT/US2020/049130.
Abdolvahabi et al., "How Do Gyrating Beads Accelerate Amyloid Fibrillization?" Biophys J, Jan. 24, 2017 (Jan. 24, 2017), vol. 112, pp. 250-264, entire document.
Giehm et al., "Strategies to increase the reproducibility of protein fibrillization in plate reader assays", Analytical Biochemistry 400 (2010) 270-281.
International Search Report and Written Opinion issued in PCT/US21/14446, mailing date Apr. 23, 2021.
United States Patent and Trademark Office, Non-Final Rejection issued in U.S. Appl. No. 17/154,431, dated Aug. 7, 2023 (16 pages).
Derose, P., "Standard Guide to Fluorescence—Instrument Calibration and Validation," NIST Interagency/Internal Report (NISTIR), Section 3-4, Jan. 2, 2008, pp. 7-10.
Concha-Marambio, L. et al., "Detection of Misfolded α-Synuclein Aggregates in Cerebrospinal Fluid by the Protein Misfolding Cyclic Amplification Platform," Alpha-Synuclein: Methods and Protocols, Methods in Molecular Biology, vol. 1948, Ch. 4, pp. 35-44.
Shahnawaz, M. et al., "Development of a Biochemical Diagnosis of Parkinson Disease by Detection of a-Synuclein Misfolded Aggregates in Cerebrospinal Fluid," JAMA Neurology, vol. 74, Issue 2, Feb. 2017, pp. 163-172.
Groveman, B. et al., "Rapid and ultra-senstitive quantitation of disease-associated α-synuclein seeds in brain and cerebrospinal fluid by αSyn RT-QuIC," Acta Neuropatholgica Communications, vol. 6, Issue 7, Feb. 9, 2018, pp. 1-10.
Manne, S. et al., "Ultrasensitive Detection of Aggregated α-Synuclein in Glial Cells, Human Cerebrospinal Fluid, and Brain Tissue Using the RT-QuIC Assay: New High-Throughput Neuroimmune Biomarker Assay for Parkinsonian Disorders," J Neuroimmune Pharmacol, vol. 14, Issue 3, Sep. 2019, pp. 423-435.
De Luca, C. et al., "Efficient RT-QuIC seeding activity for a-synuclein in olfactory mucosa samples of patients with Parkinson's disease and multiple system atrophy," Translational Neurodegeneration, vol. 8, Issue 24, Aug. 8, 2019, pp. 1-14.
Gade Malmos, K. et al., "ThT 101: a primer on the use of thioflavin T to investigate amyloid formation," Amyloid, vol. 24, Issue 1, 2017, pp. 9-12.
Paciotti, S. et al., "Are We Ready for Detecting α-Synuclein Prone to Aggregation in Patients? The Case of "Protein-Misfolding Cyclic Amplification" and "Real-Time Quaking-Induced Conversion" as Diagnostic Tools," Front Neuro., vol. 9, Article 415, Jun. 2018, pp. 1-9.

* cited by examiner

```
┌─────────────────────────────────────────────────────────────────┐
│ A method for distinguishing between and/or diagnosing PD or MSA │
│ in a subject who is exhibiting symptoms associated with both PD │
│ and MSA, the method comprising:                                 │
└─────────────────────────────────────────────────────────────────┘
                                  ↓
┌─────────────────────────────────────────────────────────────────┐
│ contacting a biological sample obtained from the subject and    │
│ comprising soluble, misfolded αS protein with a pre-incubation  │
│ mixture comprising a monomeric αS substrate and an indicator to │
│ form an incubation mixture;                                     │
└─────────────────────────────────────────────────────────────────┘
                                  ↓
┌─────────────────────────────────────────────────────────────────┐
│ conducting an incubation cycle two or more times on the         │
│ incubation mixture to form misfolded αS aggregates;             │
└─────────────────────────────────────────────────────────────────┘
                                  ↓
┌─────────────────────────────────────────────────────────────────┐
│ subjecting the incubation mixture to excitation and detecting   │
│ via indicator fluorescence emission the misfolded αS            │
│ aggregates; and                                                 │
└─────────────────────────────────────────────────────────────────┘
                                  ↓
┌─────────────────────────────────────────────────────────────────┐
│ diagnosing the subject has having PD or MSA depending on the    │
│ fluorescence emission intensity.                                │
└─────────────────────────────────────────────────────────────────┘
```

FIG. 2

DISCRIMINATING PARKINSON'S DISEASE FROM MULTIPLE SYSTEM ATROPHY USING ALPHA-SYNUCLEIN PMCA

CROSS-REFERENCE TO RELATED APPLICATIONS

This application claims priority from U.S. Provisional Patent Application No. 62/963,805, filed on Jan. 21, 2020, which is incorporated by reference herein in its entirety. This application is also a continuation in part of U.S. Nonprovisional patent application Ser. No. 14/852,475, filed on Sep. 11, 2015, which claims priority from U.S. Provisional Patent Application No. 62/049,304, filed on Sep. 11, 2014. This application is also a continuation in part of U.S. Nonprovisional patent application No. 17/011,374, filed on Sep. 3, 2020, which claims priority from U.S. Provisional Patent Application No. 62/895,535, filed on Sep. 4, 2019; U.S. Provisional Patent Application No. 63/040,144, filed on Jun. 17, 2020; U.S. Provisional Patent Application No. 63/042,679, filed on Jun. 23, 2020; U.S. Provisional Patent Application No. 63/045,593, filed on Jun. 29, 2020; U.S. Provisional Patent Application No. 63/073,420, filed on Sep. 1, 2020; and U.S. Provisional Patent Application No. 63/073,424, filed on Sep. 1, 2020. Each of these Related Applications is incorporated by reference herein in its entirety.

GOVERNMENT FUNDING

This invention was made with Government support under AG055053 and AG061069, awarded by the National Institutes of Health. The Government has certain rights in the invention.

SEQUENCE LISTING

A Sequence Listing has been submitted electronically in ASCII format and is hereby incorporated by reference in its entirety. The ASCII copy, created on Jan. 21, 2021, is named AMP-AS-USCIP.txt and is 26,724 bytes in size.

BACKGROUND

A number of degenerative brain diseases, collectively termed "synucleinopathies," involve pathological accumulation of misfolded alpha-synuclein ($\alpha$S) protein in the brain of affected subjects. Such diseases include Parkinson's disease (PD) and multiple system atrophy (MSA), among others.

PD is a long-term degenerative disorder of the central nervous system that mainly affects the motor system. Symptoms usually emerge slowly and, as the disease worsens, non-motor symptoms become more common. Symptoms may include tremor, rigidity, slowness of movement, and difficulty with walking. Cognitive and behavioral problems may also occur. While PD is currently incurable, medications exist that can help control symptoms, often dramatically.

MSA is a rare, fatal neurodegenerative disorder characterized by autonomic dysfunction, tremors, slow movement, muscle rigidity, and postural instability (collectively known as parkinsonism) and ataxia. MSA is often initially misdiagnosed and, thus, treated as PD. PD medications typically stop working in MSA patients. MSA-specific treatments do not exist. Nonetheless, knowing the correct diagnosis, as early as possible, is important. Treating symptoms of MSA, from sleep disorders, urinary and bowel issues, blood pressure issues, and the like, can vastly improve quality of life. The earlier an MSA patient is diagnosed, the earlier doctors can establish a plan of action to improve symptoms. An early diagnosis also allows patients and their families to spend quality time together and to prepare for end-of-life issues.

As used herein, a "misfolded $\alpha$S protein" is a protein that no longer contains all or part of the structural conformation of the $\alpha$S protein as it exists when involved in its typical, nonpathogenic normal function within a biological system. A misfolded $\alpha$S protein may aggregate and may exist in or as an aggregate. A misfolded $\alpha$S protein may localize in an $\alpha$S protein aggregate. A misfolded $\alpha$S protein may be a non-functional protein. A misfolded $\alpha$S protein may be a pathogenic conformer of the $\alpha$S protein.

Unfortunately, soluble, misfolded $\alpha$S protein is present in such low amounts in bodily fluids that it is very difficult to detect. Thus, current diagnoses of PD and MSA consist of clinical examination complemented by imaging techniques used mainly to rule out other forms of dementia. Recently, however, significant advances have been made in the detection of misfolded $\alpha$S aggregates (i.e., non-covalent associations of misfolded $\alpha$S protein), particularly via protein misfolding cyclic amplification (PMCA). See, e.g., US20160077111A1 (a Related Application) and, more recently, U.S. Nonprovisional patent application Ser. No. 17/011,374 (a Related Application), each of which is incorporated by reference herein in its entirety. Briefly, a biological sample (e.g., blood or cerebrospinal fluid) is contacted with a pre-incubation mixture, the pre-incubation mixture comprising a monomeric $\alpha$S protein (a "substrate"); a buffer composition; a salt; and an indicator, to form an incubation mixture. Multiple incubation cycles are conducted on the incubation mixture. Each incubation cycle comprises: (1) incubating the incubation mixture effective to cause misfolding and/or aggregation of the monomeric $\alpha$S substrate in the presence of any soluble, misfolded $\alpha$S protein present in the biological sample, and (2) physically disrupting the incubation mixture. Detection of misfolded $\alpha$S aggregate via indicator fluorescence indicates the presence of soluble, misfolded $\alpha$S protein in the biological sample. An example depiction of the PMCA process with a biological sample containing soluble, misfolded $\alpha$S protein is shown in FIG. 1.

What is needed is an $\alpha$S-PMCA method that is specific and sensitive enough to distinguish conclusively and reliably between PD, MSA, or a spectrum of aspects of both.

SUMMARY

A method is provided for distinguishing between and/or diagnosing PD or MSA in a subject who is exhibiting symptoms associated with both PD and MSA. The method comprises: (A) contacting a biological sample obtained from the subject and comprising soluble, misfolded $\alpha$S protein with a pre-incubation mixture comprising a monomeric $\alpha$S substrate and an indicator to form an incubation mixture; (B) conducting an incubation cycle two or more times on the incubation mixture to form misfolded $\alpha$S aggregates; (C) subjecting the incubation mixture to excitation and detecting via indicator fluorescence emission the misfolded $\alpha$S aggregates; and (D) diagnosing the subject as having PD, MSA, or a spectrum of aspects of both, depending on the fluorescence emission intensity. In some aspects, the incubation mixture includes one or more beads. In some aspects, the beads comprise silicon nitride ($Si_3Ni_4$). In some aspects, the beads comprise borosilicate glass.

BRIEF DESCRIPTION OF THE FIGURES

The present invention may be more readily understood by reference to the following figures, wherein:

FIG. 2 is an example flow chart of the method described herein for distinguishing between and/or diagnosing PD or MSA in a subject who is exhibiting symptoms associated with both PD and MSA.

DETAILED DESCRIPTION

Figure 1:
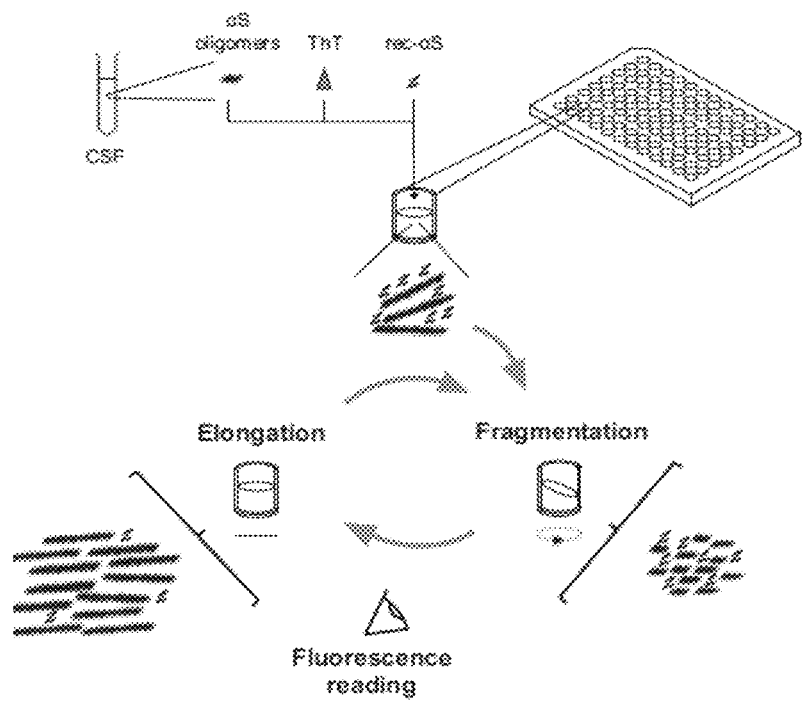
FIG. 1 is an example depiction of a PMCA process with a biological sample containing soluble, misfolded αS protein.

A method is provided for distinguishing between and/or diagnosing PD or MSA in a subject who is exhibiting symptoms associated with both PD and MSA. The method comprises: (A) contacting a biological sample obtained from the subject and comprising soluble, misfolded αS protein with a pre-incubation mixture, the pre-incubation mixture comprising: (1) a monomeric αS substrate; (2) a buffer composition; (3) a salt solution; and (4) an indicator, to form an incubation mixture; (B) conducting an incubation cycle two or more times on the incubation mixture, each incubation cycle comprising: (1) incubating the incubation mixture effective to cause misfolding and/or aggregation of the monomeric αS substrate in the presence of the soluble, misfolded αS protein; and (2) physically disrupting the incubation mixture effective to break up at least a portion of any misfolded αS aggregates formed during the incubating; (C) subjecting the incubation mixture to excitation and detecting via indicator fluorescence emission the misfolded αS aggregates; and (D) diagnosing the subject has having PD, MSA, or a spectrum of aspects of both, depending on the fluorescence emission intensity. See, e.g., FIGS. 1 and 2.

Diagnosis

The term "diagnosis" or "diagnosing" can encompass determining the likelihood that a subject will develop a disease, as well as the existence or nature of a disease in a subject. Diagnosis can also encompass diagnosis in the context of rational therapy, in which the diagnosis guides therapy, including initial selection of therapy, modification of therapy (e.g., adjustment of dose or dosage regimen), and the like.

Subjects

The terms "individual," "subject," and "patient" are used interchangeably irrespective of whether the subject has or is currently undergoing any form of treatment. The term "subject" generally refers to any vertebrate, including, but not limited to, a mammal. Examples of mammals include primates, including simians and humans, equines (e.g., horses), canines (e.g., dogs), felines, various domesticated livestock (e.g., ungulates, such as swine, pigs, goats, sheep, and the like), as well as domesticated pets (e.g., cats, hamsters, mice, and guinea pigs). Analysis of biological samples from human subjects is of particular interest.

In some aspects, the subject may be at risk of developing PD, of having PD, or being under treatment for PD; at risk of having a disease associated with dysregulation, misfolding, aggregation, or disposition of αS, such as MSA; having a disease associated with dysregulation, misfolding, aggregation, or disposition of αS; under treatment for a disease associated with dysregulation, misfolding, aggregation, or disposition of αS; and the like.

The terms "treatment," "treating," and the like, refer to obtaining a desired pharmacologic or physiologic effect. The effect may be therapeutic in terms of a partial or complete cure for a disease or an adverse effect attributable to the disease. "Treatment" covers any treatment of a disease in a mammal, particularly in a human, and can include inhibiting the disease or condition, i.e., arresting its development; and relieving the disease, i.e., causing regression of the disease.

Biological Samples

Aspects of the methods described herein may include the step of obtaining a biological sample from the subject. A "biological sample" is meant to include any biological sample from a subject that is suitable for analysis for detection of misfolded αS aggregates. Suitable biological samples include, but are not limited to, bodily fluids, such as blood-related samples (e.g., whole blood, serum, plasma, and other blood-derived samples), urine, sputum, saliva, urine, CSF, and the like. Another example of a biological sample is a tissue sample. The soluble, misfolded αS protein can be assessed either quantitatively or qualitatively, and detection of misfolded αS aggregates can be determined either in vitro or ex vivo.

A biological sample may be obtained by any known means, including needle stick, needle biopsy, swab, and the like. In an example method, the biological sample is a CSF sample, which may be obtained, for example, by lumbar puncture, in which a needle is inserted into the subarachnoid space and CSF is extracted.

In some aspects, the methods of the invention are carried out on a biological sample that is provided. A biological sample may be fresh or stored. Biological samples may be or have been stored or banked under suitable tissue storage conditions. The biological sample may be a biological sample expressly obtained for the assays as described herein or a sample obtained for another purpose that can be sub-sampled for the assays as described herein. Preferably, if stored, biological samples are either chilled or frozen shortly after collection to prevent deterioration of the sample. For example, CSF samples may be stored in polypropylene tubes at −80° C. CSF samples may be frozen in liquid nitrogen ("snap-freezing") or by placing the samples in an environment kept at −80° C., such as a cold-room or freezer.

The biological sample may be pretreated as necessary by dilution in an appropriate buffer solution, concentrated if desired, or fractionated by any number of methods, including but not limited to, ultracentrifugation, fractionation by fast performance liquid chromatography (FPLC) or HPLC, or precipitation of proteins with dextran sulfate or other methods. Any of a number of standard aqueous buffer solutions at physiological pH, such as phosphate, Tris, or the like, can be used.

Monomeric αS Substrate

As used herein, "αS" may refer to full-length, 140 amino acid alpha-synuclein protein, e.g., "αS-140." Other isoforms or fragments may include "αS-126," alpha-synuclein-126, which lacks residues 41-54, e.g., due to loss of exon 3; and "αS-112" alpha-synuclein-112, which lacks residue 103-130, e.g., due to loss of exon 5. Various αS isoforms may include, e.g., αS-140, αS-126, and αS-112.

In one aspect, the monomeric αS substrate comprises, consists essentially of, or consists of wild type or recombinant human αS protein having 140 amino acids, having a molecular mass of 14,460 Da, and being represented by the sequence:

```
SEQ ID NO. 1:
MDVFMKGLSK AKEGVVAAAE KTKQGVAEAA GKTKEGVLYV

GSKTKEGVVH GVATVAEKTK EQVTNVGGAV VTGVTAVAQK

TVEGAGSIAA ATGFVKKDQL GKNEEGAPQE GILEDMPVDP

DNEAYEMPSE EGYQDYEPEA
```

Also included are slightly modified forms of αS, such as those including a tag for purification. Thus, in one aspect, the monomeric αS substrate comprises, consists of, or consists essentially of a recombinant αS protein comprising six additional histidine amino acids (i.e., a polyHis purification tag) on the C-terminus of SEQ ID NO. 1, resulting in a molecular mass of 15,283 Da and being represented by the sequence:

```
SEQ ID NO. 2:
MDVFMKGLSK AKEGVVAAAE KTKQGVAEAA GKTKEGVLYV

GSKTKEGVVH GVATVAEKTK EQVTNVGGAV VTGVTAVAQK

TVEGAGSIAA ATGFVKKDQL GKNEEGAPQE GILEDMPVDP

DNEAYEMPSE EGYQDYEPEA HHHHHH
```

In some aspects, the monomeric αS substrate may be any of the monomeric αS substrates disclosed in U.S. Nonprovisional patent application Ser. No. 17/011,374.

In some aspects, the monomeric αS substrate may be expressed and prepared as described in Shahnawaz, M. et al. Development of a Biochemical Diagnosis of Parkinson's Disease by Detection of alpha-Synuclein Misfolded Aggregates in Cerebrospinal Fluid. JAMA Neurol 74, 163-172 (2017), which is incorporated by reference herein in its entirety.

In some aspects, the monomeric αS substrate may be expressed and prepared as described in U.S. Provisional Patent Application No. 63/026,394, which is incorporated by reference herein in its entirety.

The incubation mixture may include various concentrations of the monomeric αS substrate as a function of the total volume of the incubation mixture prior to conducting an incubation cycle. In some aspects, the incubation mixture may include the monomeric αS substrate in a concentration, or in a concentration range, of one or more of: between about 500 nM and about 500 µM; between about 1 µM and about 200 µM; between about 5 µM to about 100 µM; between about 10 µM and about 50 µM; between about 50 µM and about 75 µM; about 65 µM (i.e., about 1 mg/ml); 65 µM; between about 10 µM and about 30 µM; greater than 10 µM and less than 30 µM; about 20 µM; about 19.6 µM (i.e., about 0.3 mg/ml); or 19.6 µM.

Buffer Compositions

The incubation mixture may include various buffer compositions. The buffer composition may be effective to maintain the pH of the incubation mixture in a range from about pH 5 to about pH 9, from about pH 6 to about pH 8, from about pH 6 to about pH 7, from about pH 7 to about pH 8, about pH 7, about pH 7.4, from about pH 6.2 to about pH 6.5, including pH 6.3, 6.4, and 6.5. In some aspects, the incubation mixture comprises one or more of the buffers Tris-HCL, MES, PIPES, MOPS, BES, TES, and HEPES. In some aspects, the incubation buffer comprises PIPES in a concentration of about 100 mM, about 500 mM, about 600 mM, or about 700 mM.

Salt Solutions

In some aspects, the incubation mixture comprises salt in a given concentration. The salt may, for example, enhance signal to noise ratio in fluorescence detection. In one aspect, the salt comprises NaCl. Other suitable salts may include KCl. In one aspect, the salt, e.g., NaCl, may be present in a concentration of about 50 mM to about 1,000 mM, about 50 mM to about 500 mM, about 50 to about 150 mM, about 150 mM to about 500 mM, about 50 mM, about 150 mM, about 300 mM, about 500 mM, about 600 mM, or about 700 mM. In one aspect, the salt, e.g., NaCl, is present in a concentration of about 500 mM.

Indicators

In some aspects, the method includes the step of contacting the incubation mixture with a protein aggregation indicator to determine if a detectable amount of misfolded αS aggregate is present in the incubation mixture. The protein aggregation indicator can be characterized by exhibiting an indicating state in the presence of misfolded αS aggregate and a non-indicating state in the absence of misfolded αS aggregate. Determining the presence of the soluble, misfolded αS protein in a biological sample may include detecting the indicating state of the indicator of misfolded αS aggregate. The indicating state of the indicator and the non-indicating state of the indicator may be characterized by a difference in fluorescence. Thus, the step of determining the presence of the soluble, misfolded αS protein in a biological sample may include detecting the difference in fluorescence. In some aspects, a molar excess of the indicator may be used, the molar excess being, for example, greater than a total molar amount of the monomeric αS substrate and the soluble, misfolded αS protein in the incubation mixture.

In some aspects, the protein aggregation indicator may include one or more of: Thioflavin-T (ThT), Congo Red, m-I-Stilbene, Chrysamine G, PIB, BF-227, X-34, TZDM, FDDNP, IMPY, NIAD-4, luminescent conjugated polythiophenes, a fusion with a fluorescent protein such as green fluorescent protein and yellow fluorescent protein, derivatives thereof, and the like. A suitable protein aggregation indicator is ThT.

Incubation Conditions

The incubation mixture may be held within a suitably sized container, such as a multi-well plate having a plurality of wells. For example, the multi-well plate may include 96 wells. The wells of the multi-well plate may have a volume of from 100 µL to 1000 µL, from 150 µL to 750 µL, or from 200 µL to 350 µL. In some aspects of the invention, each well of the multi-well plate includes a single bead.

A variety of temperatures are suitable for carrying out the incubation cycles. The temperature of the incubation mixture, in each incubation cycle, at a temperature in ° C., can independently be about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or a range between any two of the preceding values, for example, between about 15° C. and about 50° C., or between about 25° C. and about 45° C., or between about 30° C. and about 42° C. In some aspects, the incubation is carried out at about normal physiological temperatures for a warm-blooded animal. In further aspects, incubating the incubation mixture is conducted at a temperature between about 35° C. and about 40° C. or between about 37° C. and about 42° C.

Misfolded αS aggregates refer to non-covalent associations of protein including soluble, misfolded αS protein. Misfolded αS aggregates may be "de-aggregated," broken up, or disrupted to release smaller fragments or aggregates, e.g., soluble, misfolded αS protein and fragmented fibrils. The catalytic activity of a collection of misfolded αS aggregate seeds may scale, at least in part, with the number of seeds in a mixture. Accordingly, disruption of misfolded αS aggregates in a mixture to release soluble, misfolded α-S protein and fragmented fibrils seeds may lead to an increase in catalytic activity for aggregation of monomeric αS substrate.

In several aspects, de-aggregating the incubation mixture may include one or more types of physical disruption selected from: shaking, sonication, stirring, freezing/thawing, laser irradiation, autoclave incubation, high pressure, homogenization, and the like. Shaking may include cyclic agitation, such as orbital agitation. The cyclic agitation may be conducted between about 50 rotations per minute (RPM) and 10,000 RPM. The cyclic agitation may be conducted between about 200 RPM and about 2000 RPM. The cyclic agitation may be conducted at about 500 RPM or about 600-800 RPM. De-aggregation of the incubation mixture may be conducted after each incubation cycle for between about 5 seconds and about 10 minutes, between about 30 seconds and about 1 minute, between about 45 seconds and about 1 minute, for about 1 minute, and the like.

The steps of incubating and de-aggregating the incubation mixture are repeated a number of times sufficient to amplify the soluble, misfolded αS protein of the sample to provide a detectable amount of misfolded α-S aggregate. The two steps of incubating the incubation mixture and de-aggregating the incubation mixture are referred to herein as the incubation cycle. The incubation cycle may be repeated between about two times and about 1000 times, between about five times and about 500 times, between about 50 times and about 500 times, between about 150 times and about 250 times, and the like. In one aspect, for the final round of the incubation cycle, it may be advantageous to skip the de-aggregation step before performing the detecting step.

The incubation cycle may be carried out for a time between about 1 minute and about 5 hours, between about 10 minutes and about 2 hours, between about 15 minutes and about 1 hour, between about 25 minutes and about 45 minutes, and the like. In some aspects, incubating the incubation mixture and de-aggregating at least a portion of the misfolded αS aggregate comprise an incubation cycle lasting from 0.3 to 1 hours. Each incubation cycle may include independently incubating and de-aggregating the incubation mixture for one or more of: incubating between about 1 minute and about 5 hours and de-aggregating between about 5 seconds and about 10 minutes; incubating between about 10 minutes and about 2 hours and de-aggregating between about 30 sec and about 1 minute; incubating between about 15 minutes and about 1 hour and de-aggregating between about 45 seconds and about 1 minute; incubating between about 25 minutes and about 45 minutes and de-aggregating between about 45 seconds and about 1 minute; and incubating about 1 minute and de-aggregating about 1 minute.

Detection

The method of diagnosis includes repeating the steps of incubating and de-aggregating the incubation mixture a number of times necessary to amplify sufficient soluble, misfolded αS protein present in the biological sample to provide an amplified incubation mixture having a detectable amount of misfolded αS aggregate. The incubation mixture may then be contacted with a fluorescent aggregation indicator, and the level of fluorescence of the amplified incubation mixture may be determined. Analysis of the amplified soluble, misfolded αS protein can discriminate between different types of neurological disorders.

The method includes the step of contacting the incubation mixture with a fluorescent aggregation indicator to provide a fluorescent response that can determine if a subject having a neurological disorder has PD, MSA, or a spectrum of aspects of both. The fluorescent aggregation indicator can be characterized by exhibiting an indicating state in the presence of misfolded αS aggregate and a non-indicating state in the absence of misfolded αS aggregate.

A suitable fluorescent aggregation indicator is ThT, which is also known as Basic yellow 1. When ThT is added to samples containing β-sheet-rich deposits, such as the cross-β-sheet quaternary structure of amyloid fibrils, ThT fluoresces strongly with excitation and emission maxima at about 435 nm (or about 440 nm, depending on the fluorometer or spectrofluorometer) and about 485 nm (or about 490 nm, depending on the fluorometer or spectrofluorometer), respectively.

ThT fluorescence is typically measured by fluorescence spectroscopy using a filter fluorometer or spectrofluorometer. In some aspects, the ThT fluorescence emission intensity may be compared to the level of a corresponding control sample when carrying out the analysis to quantify the amount of soluble, misfolded αS protein in the biological sample.

Once the ThT fluorescence level has been determined, it can be displayed in a variety of ways. For example, the levels can be displayed graphically on a display as numeric values, proportional bars (i.e., a bar graph), or any other display method known to those skilled in the art.

Fluorescence intensity is generally proportional to the concentration of the fluorophore. However, the inventors have discovered that the fibrils and/or plaque present in a subject having PD exhibit increased fluorescence relative to the fluorescence generated by the fibrils and/or plaque present in other neurological disorders. Accordingly, in some aspects, the method diagnoses the subject as having PD if the level of fluorescence is higher than that seen for fibrils and/or plaques found in control subjects and/or in subjects having a neurological disorder other than PD (e.g., other synucleinopathies, such as MSA).

In some aspects, a diagnosis of PD is provided if the level of fluorescence detected is above a certain threshold. In other aspects, the subject is diagnosed as having PD if the detected fluorescence falls within a certain range.

In some aspects, a diagnosis of MSA is provided if the level of fluorescence detected is above a certain threshold. In some aspects, a diagnosis of MSA is provided if the level of fluorescence detected is below a certain threshold. In other aspects, the subject is diagnosed as having MSA if the detected fluorescence falls within a certain range.

Thus, in some aspects, the initial average fluorescence ($AF_i$) is determined, which for a given sample is the average fluorescence over a period of time less than the period of time necessary for the monomeric αS substrate to form a detectable amount of misfolded αS aggregates in the presence of soluble, misfolded α-S protein present in the sample. For example, in some aspects, determination may be accomplished by detecting fluorescence in the sample periodically over the first 10 hours of incubation cycles. The standard deviation ($SD_i$) of $AF_i$ should then be calculated. Once $AF_i$ and $SD_i$ have been determined, the maximum fluorescence (Fmax) of the particular sample after the monomeric αS substrate has formed a detectable amount of misfolded αS aggregates in the presence of soluble, misfolded α-S protein present in the sample should be determined. In one aspect, at an excitation of 435 nm and an emission of 485 nm, if the Fmax is from about $22.2 \times SD_i + AF_i$ to $250 \times SD_i + AF_i$, the patient is diagnosed as having MSA. If the Fmax is above $250 \times SD_i + AF_i$, the patient is diagnosed as having PD. In another aspect, at an excitation of 440 nm and an emission of 490 nm, if the Fmax is from about $9.6 \times SD_i + AF_i$ to $180 \times SD_i + AF_i$, the patient is diagnosed as having MSA. If the Fmax is above $180 \times SD_i + AF_i$, the patient is diagnosed as having PD.

Neurological Disorders and Synucleinopathies

A method is provided for diagnosing PD, MSA, or a spectrum of aspects of both in a subject having a neurological disorder. A neurological disorder is any disorder of the nervous system. Examples of neurological disorders include movement disorders such as PD, autonomic nervous system diseases such as MSA, and neuropsychiatric illnesses such as Alzheimer's disease.

In some aspects, the neurological disorder is a synucleinopathy. Synucleinopathies are neurodegenerative diseases characterized by the abnormal accumulation of aggregates of αS in cells of the nervous system such as neurons, nerve fibers, and glial cells. Examples of synucleinopathies include PD, MSA, dementia with Lewy bodies, and neuroaxonal dystrophies. In some aspects, the synucleinopathy has symptoms associated with both PD and MSA, including impaired cognition, sleep disorders, and gastrointestinal tract dysfunction.

In some aspects, the sample may be taken from a subject exhibiting no clinical signs of PD or MSA. In other aspects, the biological sample may be taken from a subject exhibiting clinical signs of PD, MSA, or both. The most recognizable symptom of PD is motor-related dysfunction. However, additional symptoms include autonomic dysfunction, neuropsychiatric problems (mood, cognition, behavior, or thought alterations), sensory dysfunction (especially altered sense of smell), and sleep difficulties.

In some aspects, the method includes treating a subject diagnosed as having PD with treatment for PD and/or its symptoms. Deep brain stimulation can be used to reduce motor symptoms associated with PD. Drugs useful for treating the motor symptoms of PD include levodopa, dopamine agonists, and monoamine oxidase B inhibitors. However, additional treatments for PD continue to be developed. See Radhakrishnan D M, Goyal V, Neurol India., 66(Supplement):S26-S35 (2018) and Iarkov et al., Front Aging Neurosci.,12:4 (2020).

Supplemental Diagnostic Tests

In some aspects, the method may further comprise additional tests to confirm the α-PMCA-based diagnosis, that is, to further distinguish the misfolded αS aggregates from a patient having PD after αS-PMCA from the misfolded αS aggregates from a patient having MSA after αS-PMCA. Examples of additional tests include the use of ligands having a high affinity for one of PD or MSA misfolded αS aggregates, creating a profile of protease-resistant fragments from the misfolded αS aggregate, and evaluating the structure of the detected misfolded αS aggregate using CD, FTIR, or cryo-ET.

Examples have been included to more clearly describe a particular aspect of the invention and its associated advantages. However, there are a wide variety of other aspects within the scope of the present invention, which should not be limited to the particular example provided herein.

EXAMPLES

A. Discriminating αS Strains in PD and MSA—Blinded Study

To demonstrate that PD and MSA can be differentiated with high specificity and high sensitivity by αS-PMCA, a blinded study was conducted using CSF samples from PD, from MSA, and from HC.

1. Patient Samples

CFS samples were obtained from 94 patients clinically diagnosed with PD, 75 with MSA, and 56 HC collected from people with other neurological diseases (epilepsy, cervical spondylosis, polyneuropathy, muscular dystrophy, viral myositis, myelopathy, and hydrocephalus). Table 1 displays a summary of the demographic characteristics of the patients.

TABLE 1

Overall demographics of PD, MSA, and control individuals studied.

| | Healthy Controls (HC) | Multiple System Atrophy (MSA) | Parkinson's Disease (PD) |
|---|---|---|---|
| Number of samples | 56 | 75 | 94 |
| Age (Mean ± SD) | 60.14 ± 10.18 | 59.67 ± 6.9 | 66.78 ± 7.91 |
| Sex (M, F) | M = 28  F = 28 | M = 56  F = 19 | M = 59  F = 36 |
| Disease Duration (Mean ± SD) | N/A | 3.847 ± 2.6 | 8.13 ± 4.7 |

Most samples were collected at the Mayo Clinic. The clinical diagnoses of probable PD and MSA were made according to internationally standardized criteria, including the UK Brain Bank guidelines. CSF samples were collected in the morning using polypropylene tubes following lumbar puncture at the L4/L5 or L3/L4 interspace with atraumatic needles after overnight fasting. The samples were centrifuged at 3,000×g for 10 min at room temperature, aliquoted, and stored at −80° C. until analysis. Blood cell (red and white) counts, glucose, protein, and hemoglobin concentration were determined.

Brain tissue from PD and MSA patients was obtained from Banner Sun Health Research Institute. Control brain tissue was supplied by NDRI (National Human Tissue Resource Center). Frozen frontal cortex samples were homogenized using a tissue grinder in 10% w/v ice-cold PBS (HyClone, Cat No. SH30256.01) with Complete protease inhibitor cocktail (Roche). Presence of αS aggregates was confirmed by immunohistochemistry in free-floating sections using the anti-phosphorylated αS monoclonal antibody pSyn#64 (1:2,000; Wako) that recognizes αS phosphorylated at Ser129, as well as by thioflavin-S staining. Human samples were manipulated following the universal precautions for working with human specimens and as directed by the Institutional Review Board of The University of Texas Health Science Center at Houston (HSC-MS-14-0608).

2. Expression and Preparation of Seed-Free αS

The pET-21b plasmid carrying the coding DNA sequence for human αS containing a polyHis-tag at the C-terminal (i.e., SEQ ID NO: 2) was overexpressed in BL2(DE3) pLysS (Invitrogen) *E. coli* at 25° C. using 0.1 mM IPTG (isopropyl β-D-thiogalactoside) for 6 h. The bacterial pellets were lysed in 50 mM $NaH_2PO_4$ (pH 8.0), 300 mM NaCl, 10 mM imidazole, 1 mM PMSF, 0.1 mM TCEP [tris-(2-carboxyethyl) phosphine], and 1 mg/ml lysozyme, followed by sonication on ice. The lysate was centrifuged at 12,000×g for 15 min at 4° C., followed by ultracentrifugation at 100,000×g for 30 min at 4° C. The supernatant was filtered through 0.45 μm filter and loaded onto a nickel-affinity column (Nickel Sepharose Fast flow, GE Healthcare). Proteins were eluted using 250 mM imidazole, and monomeric αS substrate-containing fractions were dialyzed overnight at 4° C. against Phosphate Buffered Saline (PBS) pH 7.4. To remove any preformed seeds or aggregates, the protein solution was filtered through a 100-kDa cutoff filter (Amicon Ultra from Millipore), separated into small aliquots, and stored at −80° C. until use. Protein concentration was determined by BCA Assay (Pierce). Purity of the protein was evaluated by silver staining.

3. αS-PMCA

Samples of seed-free αS (SEQ ID NO: 2) at a concentration of 1 mg/mL (i.e., about 65 μM) in 100 mM PIPES, pH 6.5, 500 mM NaCl, were placed in opaque 96-well plates (Costar, REF 3916) in the presence of 5 μM of ThT at a final volume of 200 μL. For each test, 40 μL of CSF from patients and controls or 40 μL of brain homogenate (at a final concentration of 0.001%) were used. Positive controls consisted of a well-documented and previously screened healthy CSF sample spiked with pre-formed αS oligomeric seeds. Samples were subjected to cyclic agitation (1 min at 500 rpm followed by 29 min without shaking) at 37° C. The increase in ThT fluorescence was monitored at excitation of 435 nm and emission of 485 nm, periodically, using a microplate spectrofluorometer Gemini-EM (Molecular Devices, Sunnyvale, Calif.).

For serial rounds of amplification, an aliquot from the amplified material was diluted 100-fold into fresh monomeric αS substrate, and a new αS-PMCA assay was performed otherwise using the same conditions as above. This was repeated three consecutive times to obtain materials corresponding to second ("R2"), third ("R3"), and fourth ("R4") rounds of amplification. The first round of amplification corresponds to the one initiated with the biological samples (CSF or brain homogenate).

Samples at the end of the PMCA reaction were centrifuged at 20,000×g for 30 min at 4° C. The resultant supernatants were separated from the pellets. The amount of aggregated product was measured in all samples by three alternative procedures: (1) Protein quantity in pellets was measured by silver staining after SDS-PAGE; (2) dot blot analysis of sedimented materials; and (3) BCA measurements of total protein content in the supernatant fraction. For SDS-PAGE, pellets were re-suspended in PBS and separated on 12% Bis-Tris gel, and protein bands were visualized by silver staining as per the manufacturer's protocol. For dot blot, 2 µL of re-suspended pellets was spotted onto nitrocellulose membranes (Amersham Biosciences, Germany) and air dried for 30 min at room temperature. Blots were blocked with 5% w/v nonfat dry milk in Tris-buffered saline-Tween 20 (TBS-T, 20 mM Tris, pH 7.2, 150 mM NaCl, and 0.05% (v/v) Tween 20) at room temperature for 2 h. The membranes were probed with anti-αS antibody (BD Bioscience; 1:2000) and anti-rabbit horseradish peroxidase-conjugated secondary antibodies (1:5000). The blots were visualized using enhanced chemiluminescence plus western blotting detection kit (Amersham Biosciences, Piscataway, N.J.). Finally, protein concentration in supernatants was determined by BCA assay kit as per the manufacture's protocol.

Figure 3A:
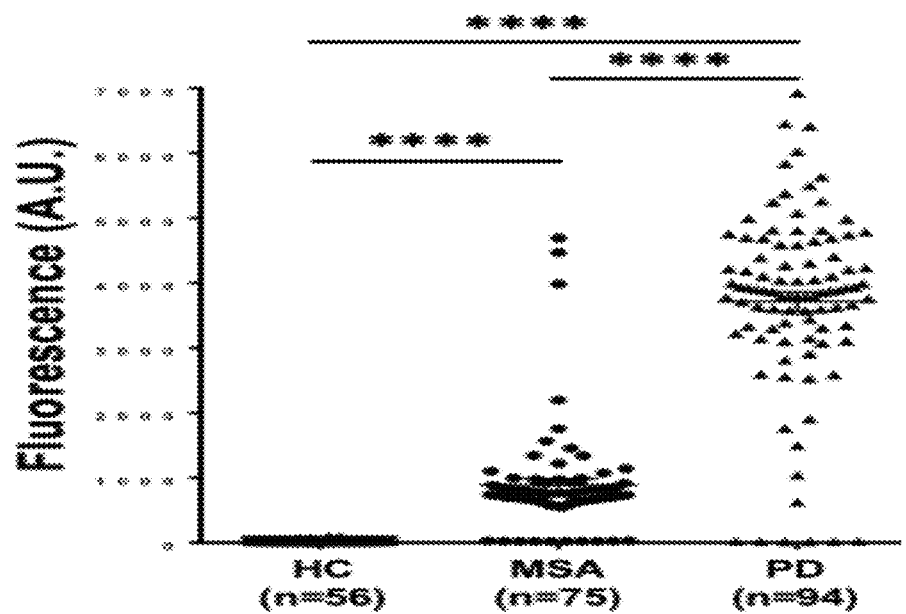
FIG. 3A is a graph showing maximum values of ThT fluorescence after αS-PMCA of PD, MSA, and healthy control (HC) patient cerebrospinal fluid (CSF) samples. Each dot represents an individual biological sample measured in duplicate.

As shown in FIG. 3A, the maximum values of ThT fluorescence after αS-PMCA from PD samples are significantly greater than MSA samples. Using a microplate spectrofluorometer Gemini-EM (Molecular Devices, Sunnyvale, Calif.) at an excitation of 435 nm and an emission of 485 nm, MSA products have a maximum fluorescence below 1800 RFU; PD ranges between 2,000 RFU and 8,000 RFU; and CSF control samples do not show any fluorescence over the background levels (FIG. 3A). Four of the 75 MSA samples exhibited kinetics of aggregation compatible with the PD strain and, conversely, three of the 94 PD samples had a profile typical of MSA. From this cohort of samples, the overall sensitivity for diagnosis of PD and MSA as compared to controls (calculated by receiving operating curves) is 93.6% and 84.6%, respectively. In both cases, specificity is 100%. Comparing differential diagnosis of PD and MSA, from the 88 clinically diagnosed PD samples showing misfolded αS aggregates by αS-PMCA, 85 were correctly identified as PD, indicating a 96.6% sensitivity. On the other hand, from the 65 MSA samples containing misfolded αS aggregates by αS-PMCA, 61 had the typical signature of MSA (maximum fluorescence below 1,800 RFU), i.e., the sensitivity to discriminate MSA from PD was 93.8%. Combining all samples, PD was correctly differentiated from MSA in 146 of the 153 samples analyzed, an overall sensitivity of 95.4%.

Figure 3B:
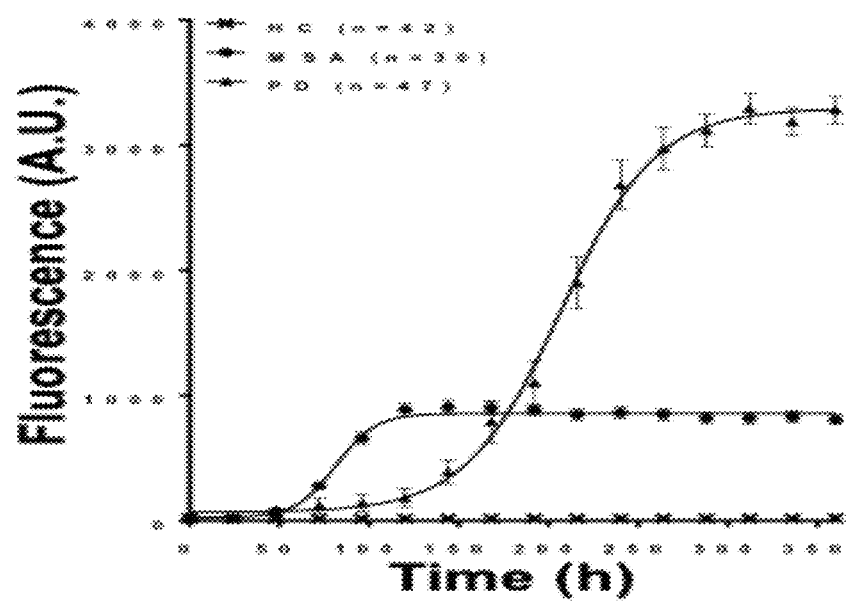
FIG. 3B is graph showing a representative aggregation curve of a subset of the data shown in FIG. 3A. All points correspond to mean±SEM of all patients analyzed in each group.

The above data was obtained in different cohorts of patients collected across distinct experiments. To illustrate the typical profile of αS-PMCA aggregation for PD and MSA samples, the largest individual cohort of samples analyzed in FIG. 3A was selected, and the data was plotted from samples identified as PD (n=47) and MSA (n=30) in FIG. 3B. The maximum fluorescence and kinetics of aggregation were consistently different for PD and MSA, with MSA aggregating faster but reaching a lower fluorescence plateau than PD (FIG. 3B).

Figure 3C:
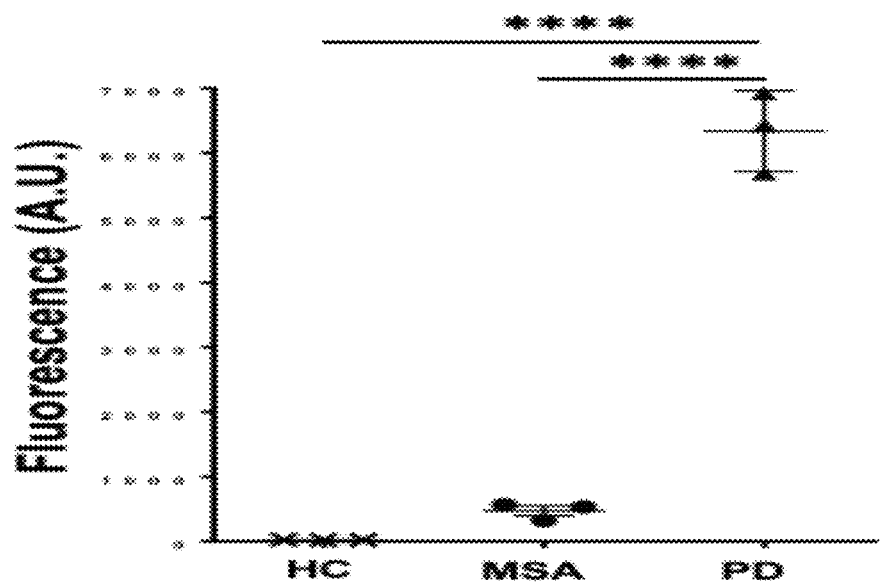
FIG. 3C is a graph showing maximum values of ThT fluorescence after αS-PMCA of PD, MSA, and HC patient brain homogenate samples. Each dot represents an individual biological sample measured in duplicate.
Figure 3D:
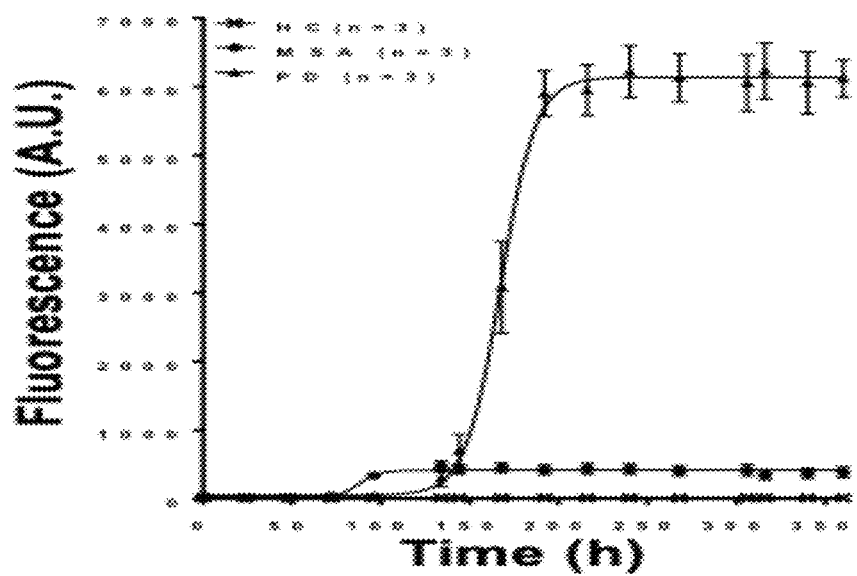
FIG. 3D is a graph showing the aggregation curve of the data shown in FIG. 3C. All points correspond to mean±SEM of all patients analyzed in each group.

To determine whether the aggregates present in CSF represent those found in the brain, brain samples from three PD or MSA patients were amplified. To avoid interference from other brain components in the reaction, the PMCA assay was started with a $10^{-4}$ dilution of brain homogenate. Under these conditions, amplification of brain-derived αS aggregates showed the typical signature of PD or MSA, both in terms of the maximum ThT fluorescence (FIG. 3C) and the kinetics of aggregation (FIG. 3D). These results suggest that the aggregates present in CSF reflect faithfully the aggregates in the patients' brains.

4. Serial αS-PMCA Amplification

Figure 4:
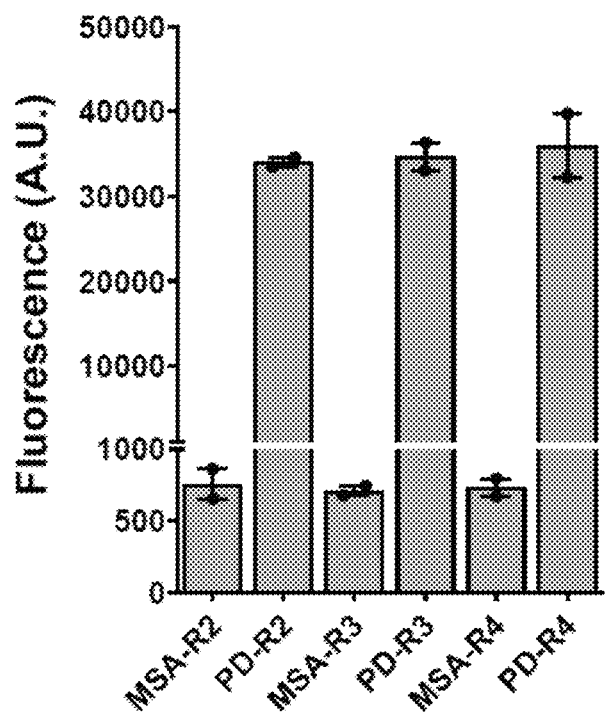
FIG. 4 is a graph showing the fluorescence of MSA- and PD-derived αS aggregates after serial αS-PMCA propagation.

The qualitative differences in ThT fluorescence were maintained when the αS-PMCA reaction products (e.g., misfolded ΔS aggregates) amplified from PD or MSA CSF were replicated serially at the expense of monomeric αS substrate (FIG. 4). For these studies, an aliquot from the amplified PD or MSA CSF was diluted 100-fold into fresh monomeric αS substrate, and a new αS-PMCA assay was performed. This was repeated several times, and the product maintained the relatively high fluorescence signal for PD and relatively low fluorescence signal for MSA (FIG. 4).

To further study the properties of the misfolded αS aggregates amplified from PD or MSA patients, sufficient material was generated from the second round of amplification from 43 PD and 43 MSA samples. The selection of the 43 samples from each disease was performed by eliminating the samples that did not aggregate (false negatives) and including those that have the typical PD or MSA signatures, as indicated above (FIG. 3B). The majority of the characterization studies were done with samples from the second cycle of amplification.

5. Measurement of Protein Concentration in the Aggregated Product After Amplification To rule out that the differences in ThT fluorescence simply reflect distinct amounts of misfolded αS aggregates at the end of the reaction, sedimentation assays were performed to separate the pools of soluble and aggregated αS. The amount of protein pelleting after centrifugation at 20,000×g for 30 min was measured using silver staining after SDS-PAGE and dot blot analysis. The amount of protein remaining in the supernatant was measured using the BCA kit. The amount of aggregates produced at the end of the αS-PMCA assay was the same in both PD and MSA samples. Thus, either the accessibility or the mode of interaction of ThT with PD or MSA aggregates is distinct and reflects the structural differences between them.

6. Interaction of αS Aggregates with Thiophene-Based Ligands

A panel of thiophene-based ligands was used to study in more detail the differences between PD and MSA aggregates. The conjugated thiophene backbone is flexible, and thus, the binding and fluorescence emission of the molecules depends on the conformational properties of the aggregates, providing a specific spectral fingerprint of different aggregates.

Thus, seven different thiophene-based ligands (p-FTAA, h-FTAA, HS-68, HS-167, HS-169, HS-194 and HS-199) were analyzed. The compounds were synthetized and characterized as described previously (Shirani et al., Chemistry 23, 17127-17135 (2017); Shirani, et al., Chemistry 21, 15133-15137 (2015)), or as outlined below for compound HS-199. The stock solution for each compound was prepared in de-ionized water or DMSO at 1.5 mM. These stocks were diluted to reach a final concentration of 150 µM.

Figure 5A:
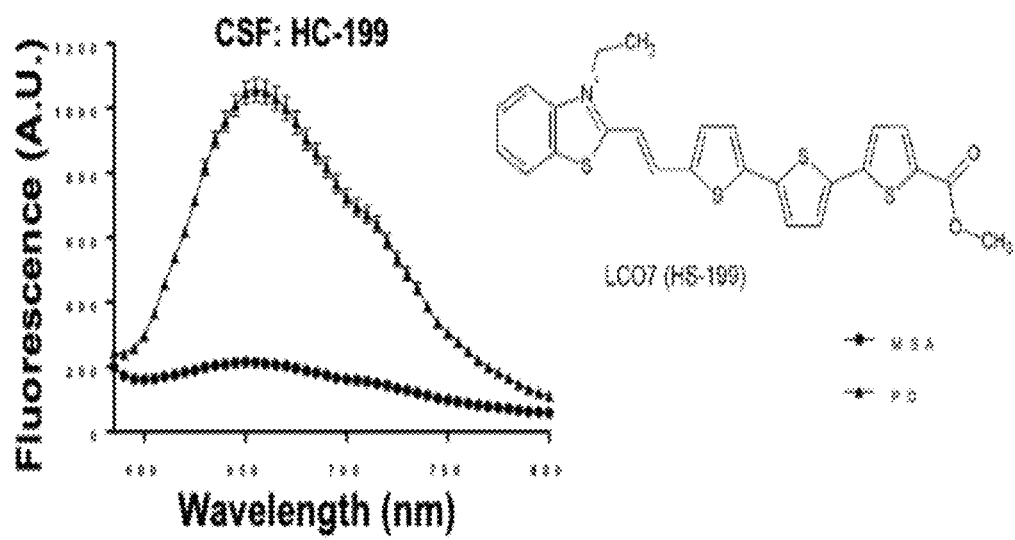
FIGS. 5A and 5B are graphs showing relative binding and fluorescence emission of thiophene ligand HS-199 in the presence of misfolded αS aggregates derived from PD or MSA patients' CSF (FIG. 5A) or brain extracts (FIG. 5B) after αS-PMCA.
Figure 5B:
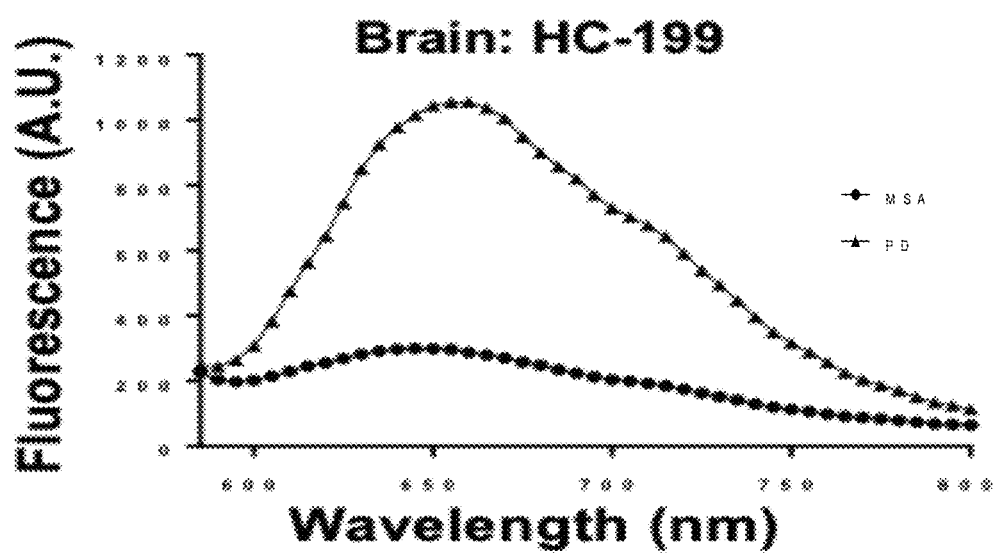
Figures 5C, 5D:
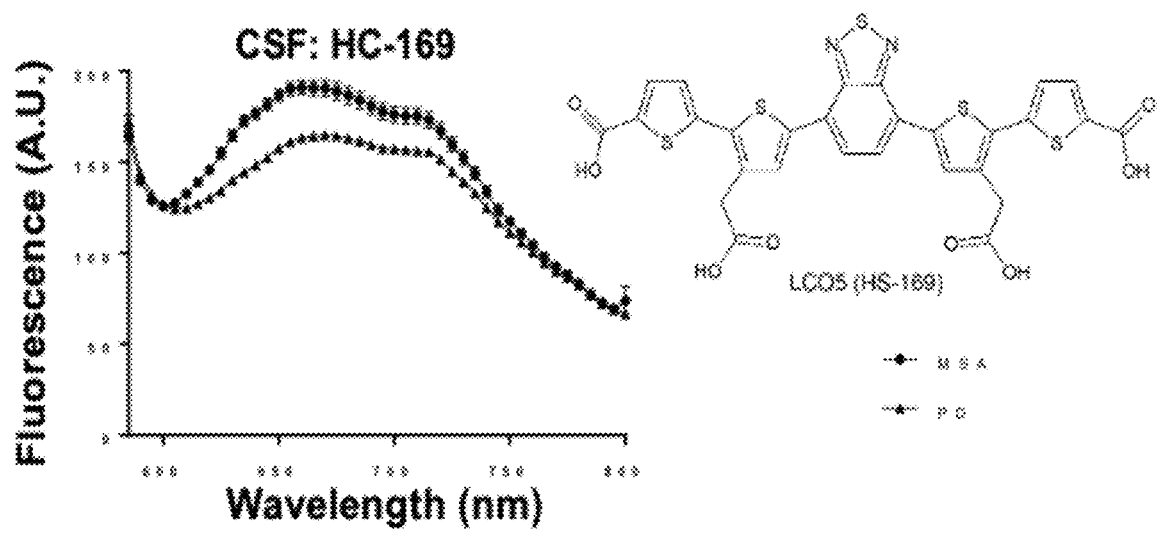
FIGS. 5C and 5D are graphs showing relative binding and fluorescence emission of thiophene ligand HS-169 in the presence of misfolded αS aggregates derived from PD or MSA patients' CSF (FIG. 5C) or brain extracts (FIG. 5D) after αS-PMCA.

The thiophene-based ligands showed substantially different capacities to interact with αS aggregates derived from PD and MSA samples (FIGS. 5A-5D). For example, HS-199 showed a very specific binding and high fluorescence emission for PD aggregates, whereas the dye fluorescence in the presence of MSA aggregates was very low (FIG. 5A). Similar results were obtained when analyzing samples derived from brain extracts for these diseases (FIG. 5B), further supporting the conclusion that aggregates amplified from CSF and brain are equivalent. Conversely, the HS-169 dye appeared to bind preferentially to MSA aggregates as compared to PD aggregates, whether amplified from CSF (FIG. 5C) or brain (FIG. 5D).

7. Synthesis and Characterization of HS-199

A mixture of Methyl 5'-bromo-[2,2'-bithiophene]-5-carboxylate (140 mg, 0.462 mM) ("a" below), (5-formylthiophen-2-yl)boronic acid (80 mg, 0.508 mM) ("b" below), $K_2CO_3$ (192 mg, 1.39 mmol) in 1,4-dioxane/methanol (8:2,8 mL/mM, degassed), and PEPPS-IPr (2 mol %) was heated to 80° C. for 30 min. After cooling to room temperature, the pH was adjusted to 4 by 1 M HCl, and the residue was extracted with DCM (3×20 ml/mM), washed with water (3×20 ml/mM), and washed with brine (30 ml). The combined organic phase was dried over $MgSO_4$, and the solvent was evaporated. The residue was subjected to column chromatography using $CH_2Cl_2$, followed by crystallization from DMF to yield a trimer ("c" below) as a yellow solid (115 mg, 74%). A few drops of pyridine were added to a cold solution of the trimer (0.05 g, 0.150 mM) and 2-methyl-3-alkylbenzothiazolium salt ("d" below) (46 mg, 150 mM) in an anhydrous mixture of MeOH/THF (8:2). The mixture was refluxed until completion of the reaction (monitored by TLC, eluent: DCM/MeOH 1%). The solvent was evaporated under vacuum to provide a dark red solid, which was crystallized from MeOH. The red crystals were collected by filtration, washed with cold MeOH, and dried in vacuum to afford HS-199 as a dark red solid (53 mg, 57%).

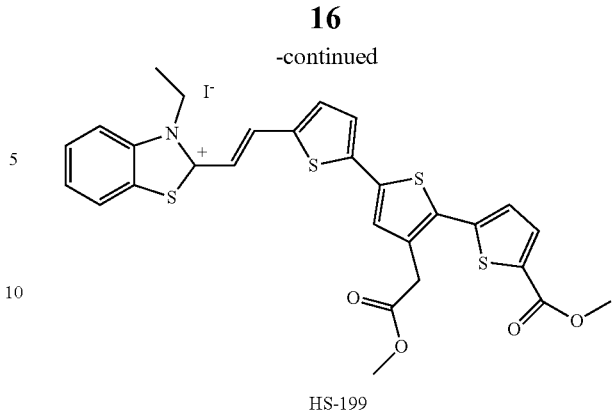

HS-199

The compound was characterized by infra-red (IR) spectroscopy, NMR, and mass spectrometry. IR (neat) 1697, 7594, 1582, 1525, 1446, 1421, 1304, 1245, 1210, 1165, 1098, 1054, 1035, 926, 806, 786, 758, 744 cm$^{-1}$. $^1$H NMR (300 MHz, DMSO-d6) δδ 8.48-841 (m, 2H), 8.27 (d, J=8.6 Hz, 1H), 7.97 (d, J=3.9 Hz, 1H), 7.91-7.58 (m, 7H), 7.50 (d, J=3.9 Hz, 1H), 4.92 (q, J=7.0 Hz, 2H), 3.85 (s, 3H), 1.47 (t, J=7.0 Hz, 3H). $^{13}$C NMR (75 MHz, DMSO-d6) δ 170.53, 161.43, 143.01, 142.17, 140.89, 140.83, 138.37, 137.10, 136.14, 136.01, 134.89, 131.30, 129.48, 28.26, 128.16, 127.79, 127.69, 126.66, 125.58, 124.38, 116.44, 111.21, 52.41, 44.29, 14.14. MALDI-TOF: m/z calculated for $C_{25}H_{20}NO_2S_4$ (M+H)$^+$: 495.0. Found: 495.0.

8. Protease Digestion and Epitope Mapping

Figure 6A:
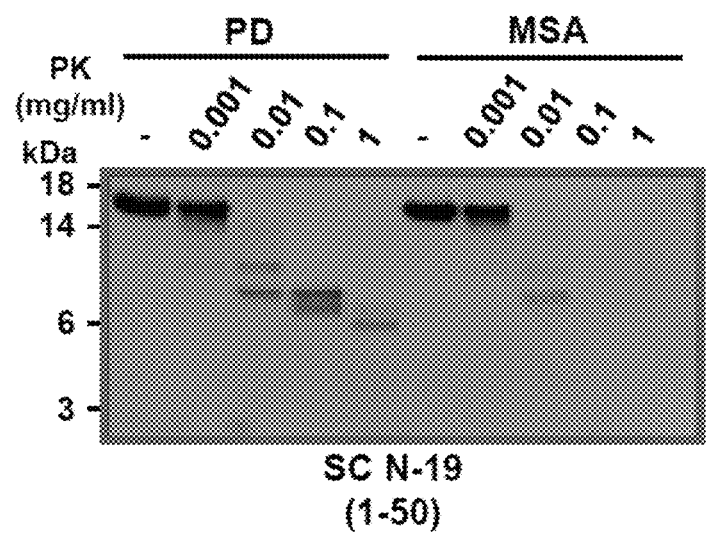
FIGS. 6A-6C provide images showing protease-resistance and epitope mapping of misfolded αS aggregates derived from PD or MSA patients' CSF after αS-PMCA.
Figure 6B:
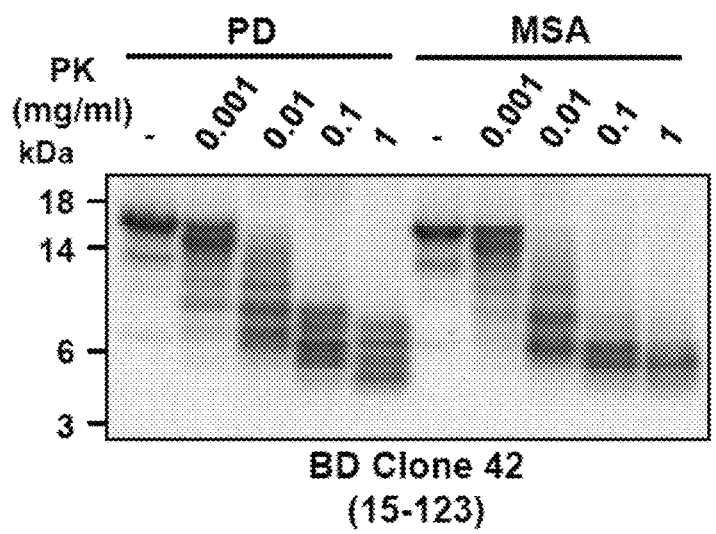
Figure 6C:
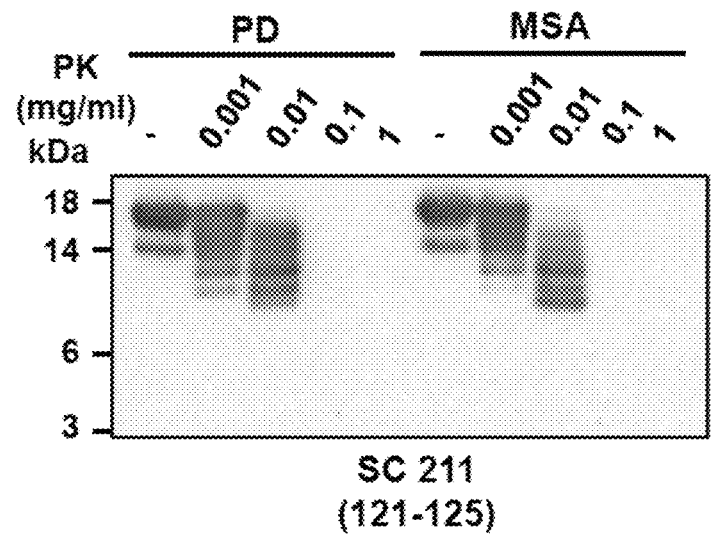

To analyze biochemical differences between PD- and MSA-derived αS aggregates, experiments were performed to test resistance to proteolytic degradation and epitope mapping. Thus, samples containing αS aggregates amplified by PMCA were treated with different concentrations of proteinase K (PK) at 37° C. for 1 h. The reaction was stopped by heating the sample in NuPAGE LDS buffer at 95° C. for 10 min. The digested products were resolved by 12% Bis-Tris gels (Invitrogen). Proteins were electrophoretically transferred to nitrocellulose membranes (Amersham Biosciences). Membranes were blocked with 5% w/v nonfat dry milk in phosphate-buffered saline-Tween 20 (PBS (Hyclone SH.30258.02, pH 7.2, 0.1% (v/v) Tween 20) at room temperature for 1 h. After blocking, the membranes were probed with the following antibodies: N-19 from Santa Cruz, reactive against the N-terminus (residues 1-50) of αSyn (FIG. 6A); anti-αS clone 42 from BD Biosciences, reactive against the middle region (aa 15-123) of the protein (FIG. 6B); and 211 from Santa Cruz, reactive against the C-terminal region (121-125) of αS (FIG. 6C). The blots were developed using ECL Prime Detection Western Blotting Reagents (Amersham Biosciences).

αS aggregates derived by seeding/amplification from the CSF of patients affected by PD or MSA differed in the extent of protease resistance and the size of the core fragment resistant to degradation, as analyzed by a panel of different sequence antibodies (FIGS. 6A-6C). αS aggregates amplified from PD or MSA were very resistant to degradation, even after treatment with a high concentration of PK (1 mg/ml) for 1 h. Under these conditions, proteolysis resulted in protease-resistant fragments mostly mapping to the N-terminal (FIG. 6A) and middle region (FIG. 6B) of the protein. On the contrary, the C-terminal region of αS appears to be fully degraded after incubation with >0.01 mg/ml of PK (FIG. 6C), suggesting that this part of the protein may not be implicated in the aggregate formation.

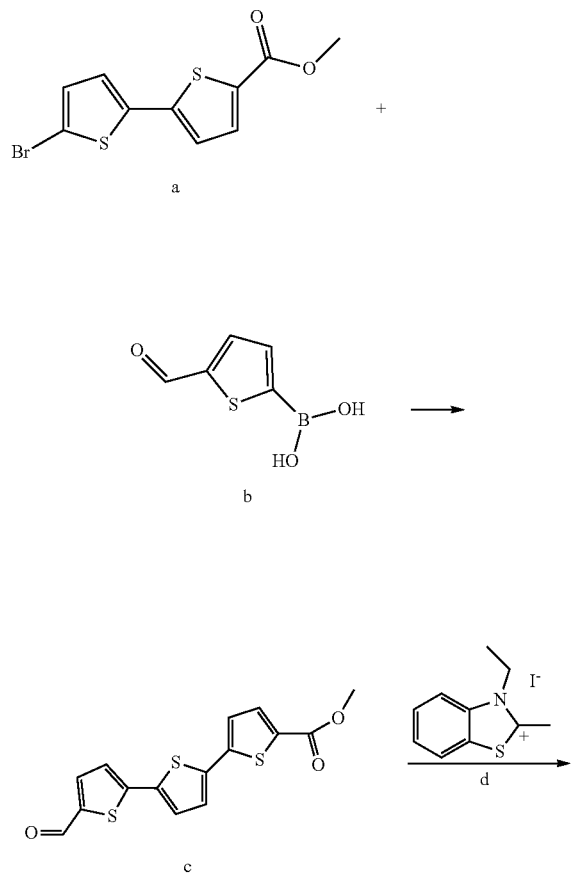

Figure 6D:
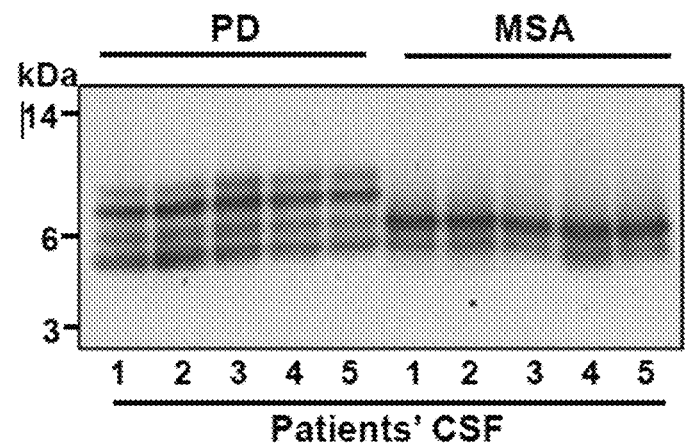
FIGS. 6D-6F provide images showing the size and number of protease resistant bands detectable by antibodies directed to the middle region (residues 15-123) of misfolded αS aggregates derived from PD or MSA patients' CSF after two rounds of αS-PMCA (FIG. 6D), after serial replication (FIG. 6E), and after αS-PMCA of brain extracts (FIG. 6F).
Figure 6E:
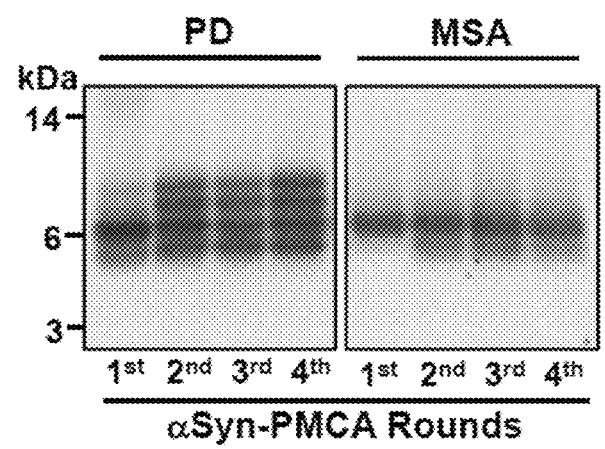
Figure 6F:
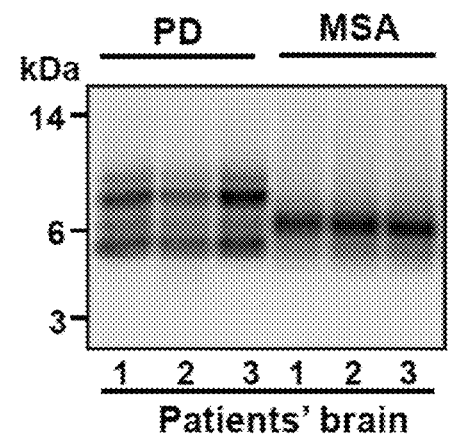

The size and number of protease resistant bands detectable by antibodies directed to the middle region (residues 15-123) of the αS aggregates substantially differed between PD and MSA products. Four bands with molecular weights ranging between 4-10 kDa were detected for PD vs. only two bands (4 and 6 kDa) for MSA samples (FIGS. 6B and 6D). This signature was observed on all 43 different PD and MSA samples analyzed (FIG. 6D shows five representative samples per disease). This signature was maintained upon serial replication in vitro by αS-PMCA (FIG. 6E), albeit with some small variability on the relative proportion of different bands among distinct rounds of amplification. This result provides further evidence that αS-PMCA faithfully maintains the biochemical and structural properties of αS aggregates. The pattern of PK resistance of αS aggregates amplified from the brain of patients was also analyzed. As shown in FIG. 6F, the profile of protease-resistant fragments from brain exhibited the typical signature of PD or MSA, reinforcing that the aggregates present in CSF readily reflect those accumulated in the patients' brains.

9. Circular Dichroism (CD)

Secondary structures were studied by CD. Solutions containing ~35 μM of αS aggregates amplified by αS-PMCA were used. CD spectra were recorded at room temperature using a JASCO J815 spectropolarimeter, with 1 mm path length cuvette. CD data was collected at 0.1 nm resolution and at a 200 nm/min scan speed. The portion of the CD spectrum between 250-350 nm was fit with a quadratic function, and the baseline of the whole spectrum was calculated using the function. The calculated baseline was subtracted from the CD spectrum to obtain baseline-corrected CD spectrum.

Figure 7A:
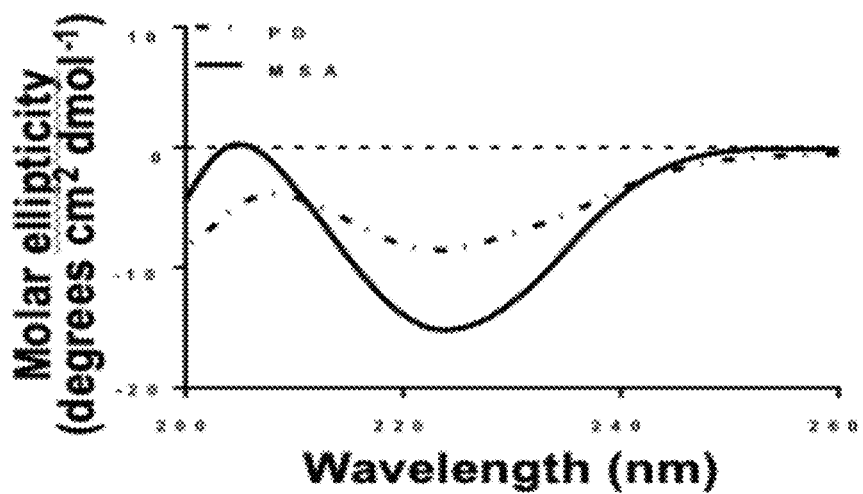
FIGS. 7A and 7B are graphs showing circular dichroism (CD) spectra of misfolded αS aggregates derived from PD or MSA patients' CSF (FIG. 7A) and brain extracts (FIG. 7B) after αS-PMCA.
Figure 7B:
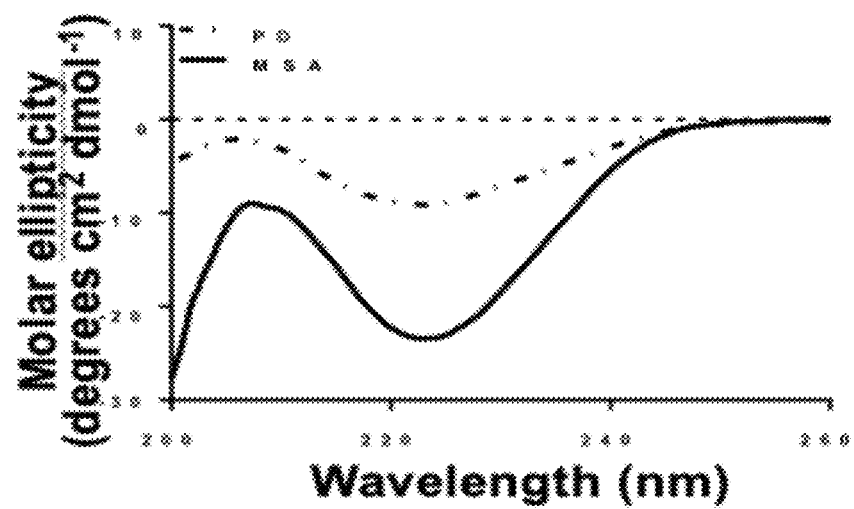

The CD spectroscopy showed that both PD and MSA aggregates exhibit a predominant β-sheet structure, as illustrated by a negative peak at around 220 nm (FIG. 7A). MSA samples appear to have a higher proportion of β-sheet structure than PD samples. Analogous results were obtained in all three of the PD and MSA samples amplified from the brain of these patients (FIG. 7B).

10. Fourier-Transformed Infrared Spectroscopy (FTIR)

To confirm the CD results using a different methodology, the secondary structure composition was estimated by FTIR spectroscopy of a randomly selected group of 10 PD and 10 MSA samples. FTIR experiments were conducted in an FT/IR-4100 spectrometer from JASCO. The product of αS-PMCA (5 μL) was placed on the top of a diamond PRO450-S Attenuated Total Reflectance unit from JASCO adapted to the FT/IR-4100 system. System parameters included 4.0 $cm^{-1}$ resolution and an accumulation of 80 scans per sample. The data were processed using cosine apodization and Mertz phase correction. The data were also corrected for attenuated total reflectance and carbon dioxide vapor absorption.

Figure 8:
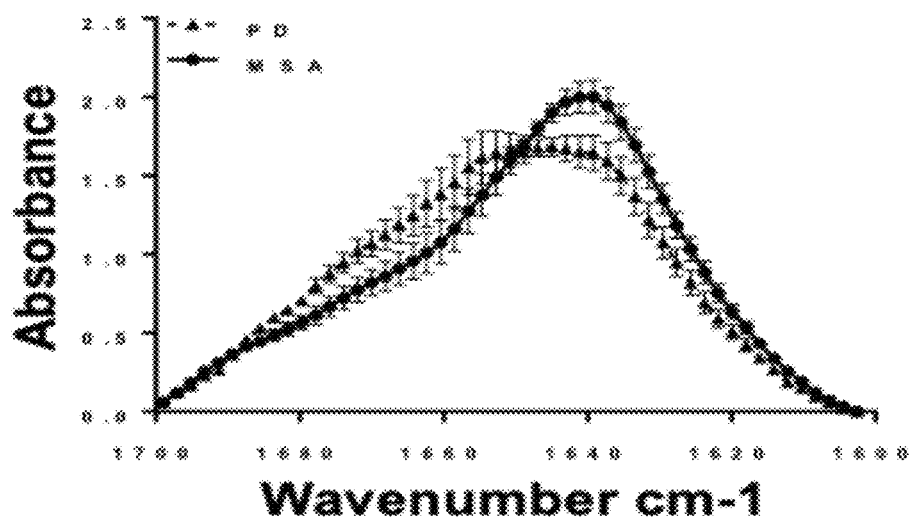
FIG. 8 is a graph showing Fourier-transformed infrared (FTIR) spectra of misfolded αS aggregates derived from PD or MSA patients' CSF after αS-PMCA.

The results for MSA derived aggregates showed spectra dominated by parallel β-sheet structure (peak at 1640 $cm^{-1}$). For PD-derived aggregates, there was also another clear peak at ~1652 $cm^{-1}$, which can be assigned to either an a-helix or a random coil (FIG. 8).

11. Cryo-Electron Tomography (Cryo-ET) Analysis and 3D Reconstructions

To gain further insight into the structures of both αS species, cryo-ET studies were performed. Cryo-ET takes multiple shots in the same area by tilting the sample in a series of angles. A 3D tomogram can be directly reconstructed from the multiple tilt series. To increase tomographic image contrast, the fibrils amplified from the CSF of patients affected by PD and MSA were negatively stained. 17 and 22 tilt series were taken for PD and MSA specimens, respectively.

The product of αS-PMCA derived from the CSF of PD or MSA samples subjected to two rounds of amplification was sedimented at 20,000×g for 30 minutes at 4° C., resuspended in 100 mM PIPES, pH 6.5, 500 mM NaCl, diluted 10-fold in deionized water, and loaded onto Formvar/Carbon Copper grids. Samples were negatively stained with 2% uranyl acetate and rapidly frozen in liquid ethane, using a gravity-driven plunger apparatus. Materials were imaged at −170° C. using a Polara G2 electron microscope (FEI Company) equipped with a field emission gun and a direct detection device (Gatan K2 Summit). The microscope was operated at 300 kV with a magnification of ×15,500. SerialEM (Mastronarde, D. N., J Struct Biol 152, 36-51 (2005)) was used to collect tomographic tilt series at ~6 μm defocus with cumulative doses of ~200 $e^-/Å^2$. For each dataset, 35 image stacks were collected in a range from −51° to +51°, using increments of 3°. Each stack contained about 10 images, which were first aligned using MotionCor2. The tomograms were reconstructed using IMOD software and were further processed by EMAN software.

The helical models were manually built based on individual fibril density. The twist lengths of fibrils vary from one to another. Helical parameters (diameter and the twist lengths), which can be directly measured from the center slice of the tomogram in X-Y plane, were used to build a helical model. Instead of creating a mathematical helical model based on the two parameters, the helical model was manually built by tracing the filament density using Chimera software. Model dots were placed along the densities, followed by manual adjustment of the dot positions to make the model shape helix-like under the restriction of cryo-ET density.

Figure 9A:
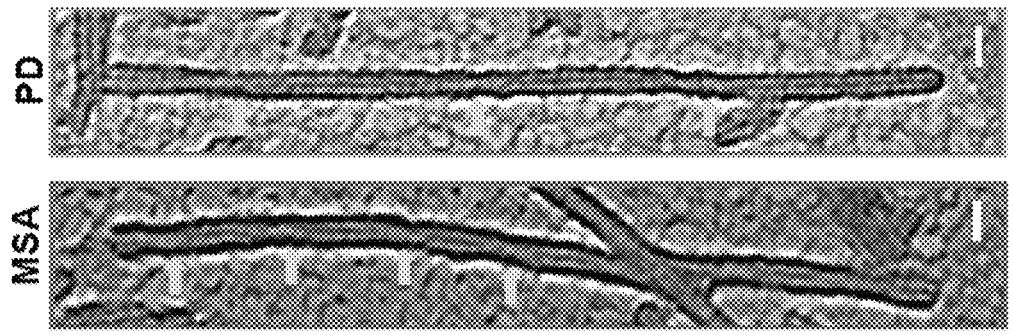
FIGS. 9A and 9B show the cryo-electron topography (Cryo-ET) tomograms of misfolded αS aggregates derived from PD or MSA patients' CSF after αS-PMCA.
Figure 9B:
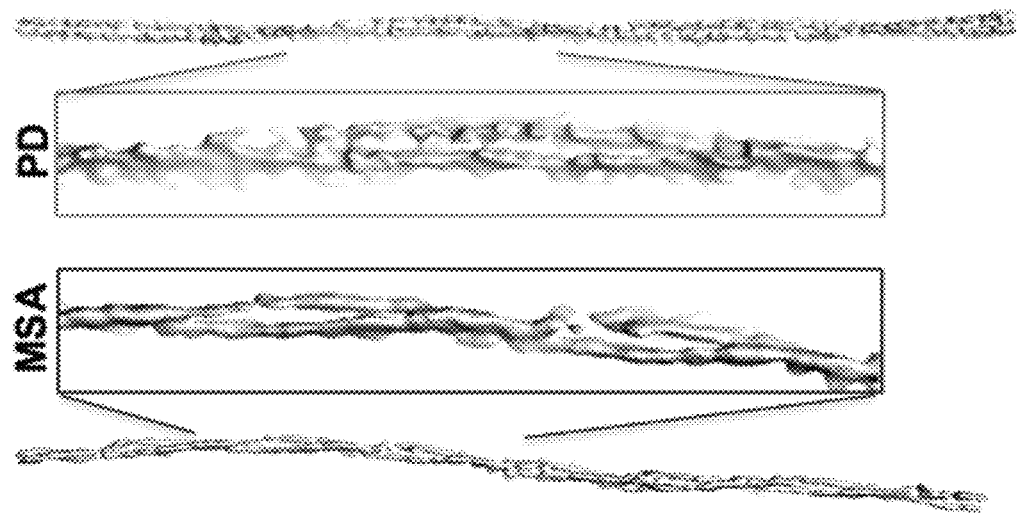
Figure 9C:
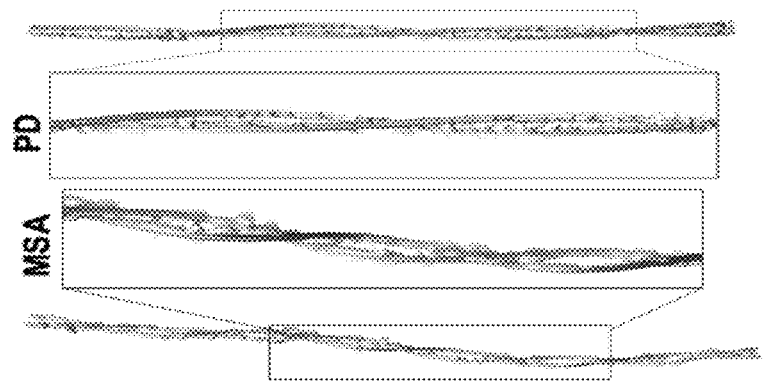
FIGS. 9C and 9D show helical models manually built by reference to the Cryo-ET tomograms shown in FIGS. 9A and 9B.
Figure 9D:
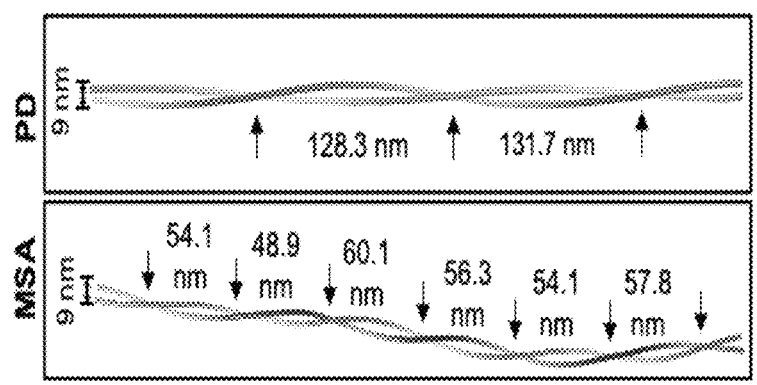
Figure 9E:
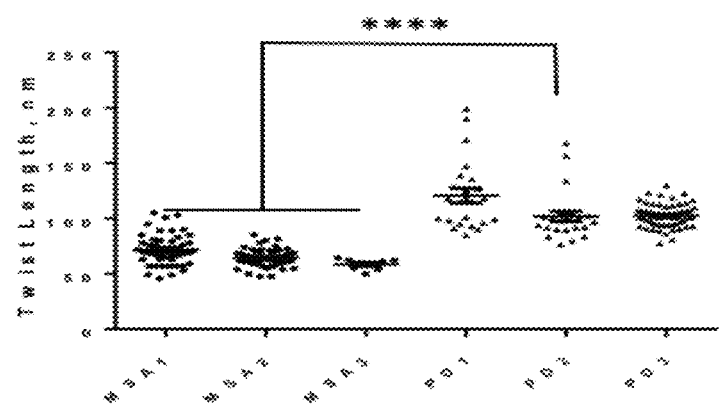
FIG. 9E shows a plot of periodic helical twist spacing in MSA and PD fibrils based on measurements taken from the helical model shown in FIG. 9D.

The tomograms (FIGS. 9A and 9B) have enough contrast to recognize that both fibrils are composed of two protofilaments intertwining in a left-handed helix with a diameter of ~9 nm, in agreement with the high-resolution structure obtained by cryo-EM for full-length αS aggregates prepared in vitro. However, the lengths of fibril twists clearly vary between PD and MSA aggregates. Based on the individual measurements of the helical diameter and twist lengths, helical models were manually built (FIGS. 9C and 9D) guided by the segmented fibril densities (FIG. 9D). PMCA-derived αS aggregates from PD patients were made of long stretches of straight filaments with helical twists predominantly ranging from 76.6-199 nm (FIG. 9D). In contrast, PMCA derived αS filaments from MSA patients have shorter twists, predominantly ranging from 46-105 nm (FIG. 9D). Indeed, measurements of periodic spacing in MSA fibrils (n=104 from 3 different patients) indicated an average twisting distance of 65.2 ±3.8 nm (mean±SEM), whereas the average periodic spacing for PD fibrils (n=104 from 3 different patients) was 108.5±6.1 nm (FIG. 9E). The difference between the periodic spacing of PD and MSA fibrils was statistically significant. Thus, the structures of αS aggregates derived from PD or MSA are different based at least on their average periodicities of helical twists.

12. Cytotoxicity Assays

To explore if αS aggregates derived from the CSF of PD or MSA patients have biological differences, their toxicity in cell culture was studied. For these experiments, RK13 and a human neuronal precursor cells differentiated from induced pluripotent stem cells (iPSCs) were used. iPSCs and neuronal precursors were generated and characterized from fibroblasts obtained from a healthy individual. Cytotoxicity was tested by incubating the cells with different concentrations of αS aggregates derived from PD or MSA CSF.

Thus, RK13 cells (rabbit kidney cell line, ATCC CCL-37) were grown in DMEM media supplemented with 10% FBS 1× GLUTAmax, 1× MEM, 1 mM sodium pyruvate. For toxicity, 10,000 cells were plated without antibiotic in a 96-well plate and incubated at 37° C. for 24 h. Neuronal precursors derived from human iPSCs were generated and characterized as previously described. Armijo et al., Neurosci. Lett 639, 74-81 (2017). These cells were maintained in neural precursor expansion medium. Approximately 20,000 cells were plated per well in a 96-well plate, precoated with Geltrex LDEV-free reduced growth factor basement membrane matrix treated dishes (1:100, Invitrogen), and incubated at 37° C. for 24 h. After 24 h, cells were treated for either 24 h (RK 13 cells) or for 48 h (neuronal precursors) with different concentrations of amplified αS fibrils originated from CSF samples of MSA and PD patients. Cell viability was determined by the MTT assay, following the manufacturer's protocol.

Figure 10A:
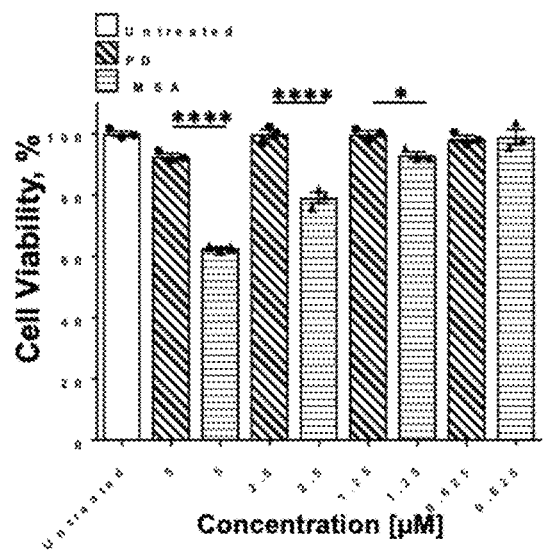
FIGS. 10A and 10B provide graphs showing the cytotoxicity of misfolded αS aggregates derived from PD or MSA patients' CSF after αS-PMCA vis-à-vis RK-13 (FIG. 10A) or neuronal precursors derived from human iPSCs (FIG. 10B).
Figure 10B:
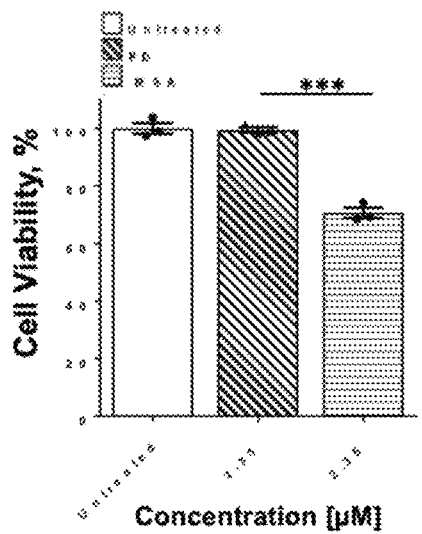

MSA aggregates produced highly significant toxicity in RK13 cells, even at concentrations of 1.25 µM, whereas PD derived aggregates began to show significant toxicity only at 5 µM (FIG. 10A), indicating that MSA aggregates are more toxic than PD aggregates. A similar conclusion was obtained in neuronal precursors cells derived from human iPSCs (FIG. 10B).

B. Discriminating αS Strains in PD and MSA Using Beads

1. αS-PMCA of PD and MSA CSF Samples

PD and MSA CSF samples were run under the following conditions:

| Parameter | Fast Assay (FA) |
|---|---|
| Buffer ([ ] (mM) and pH) | 100 mM PIPES pH 6.5 [Sigma, cat# 80635-50G] |
| [NaCl] (mM) | 500 [Lonza, cat# 51202] |
| ThT (µM) | 10 [Sigma, cat# T3516-25G] |
| Substrate | Recombinant C-terminal histag αSyn (MW = 15,283 mg/mmol) (SEQ ID NO: 2) |
| [substrate] (µM) | 19.6 µM |
| [substrate] (mg/mL) | 0.3 (19.6 µM) |
| CSF sample (µL) | 40 |
| Shaking type | Orbital |
| Shaking speed (rpm) | 800 |
| Shaking time (min) | 1 |
| Incubation time (min) | 29 |
| Beads material | $Si_3N_4$ |
| Beads size (mm) | 2.38 (3/32") |
| Amount of beads | 1 (ea) |
| Temperature (° C.) | 37 |
| Reaction volume (µL) | 200 |

The beads are manufactured by Tsubaki-Nakashima. The beads were blocked with a solution of bovine serum albumin (BSA) in PIPES (1% BSA in 100 mM PIPES pH 6.50) prior to use.

The assay was assembled in 96 well ELISA plates [Corning, cat #3916]. One bead was added to each well, and the plate was covered with a pierceable optical film [Excel Scientific, cat #XP-100] to avoid cross-contamination while preparing the assay. After all of the PMCA reactions were pipetted into the plate, the pierceable optical film was removed, and a fluorescent-compatible film was used to cover the plate (Applied Biosystems, cat #4311971).

The plate was transferred to a FLUOstar® Omega Microplate Reader [BMG], an instrument that shakes, incubates, and reads fluorescence automatically. The plate was orbitally shaken at 800 rpm for 1 minute, read (440-10 excitation and 490-10 emission), and incubated at 37° C. The plate was shaken for 1 minute every 29 minutes, which constitutes an αS-PMCA cycle of 30 minutes.

Figure 11A:
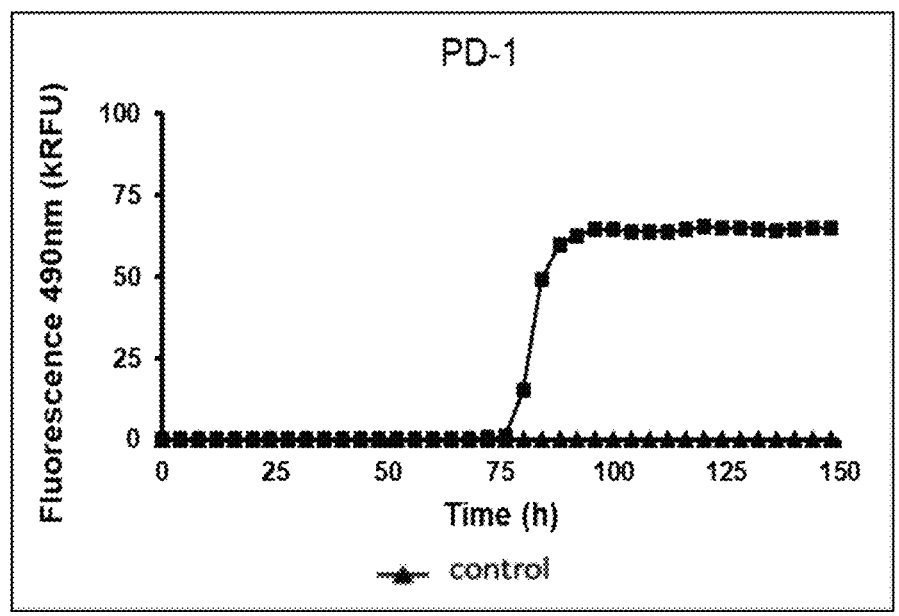
FIG. 11A shows an aggregation curve for αS-PMCA of a PD patient's CSF where beads were included in the incubation mixture. The patient presents pure PD pathology.
Figure 11B:
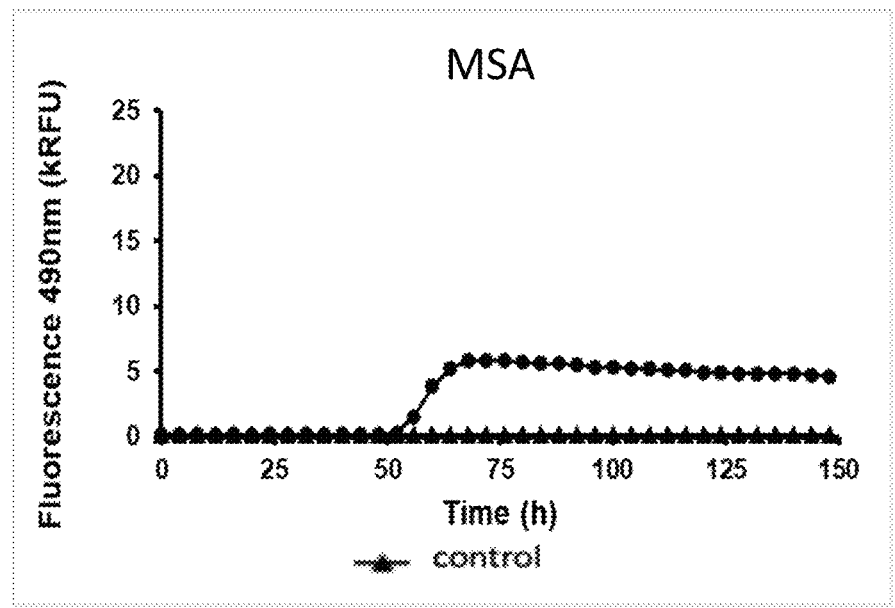
FIG. 11B shows an aggregation curve for αS-PMCA of an MSA patient's CSF where beads were included in the incubation mixture. The patient presents pure MSA pathology.

FIG. 11A shows an aggregation curve for αS-PMCA of a PD patient's CSF where beads were included in the incubation mixture. The patient presents pure PD pathology. FIG. 11B shows an aggregation curve for αS-PMCA of an MSA patient's CSF where beads were included in the incubation mixture. The patient presents pure MSA pathology. The maximum fluorescence and kinetics of aggregation were consistently different for PD and MSA, with MSA aggregating faster but reaching a much lower fluorescence plateau than PD.

2. Serial αS-PMCA Amplification of PD and MSA CSF Samples

Figure 12A:
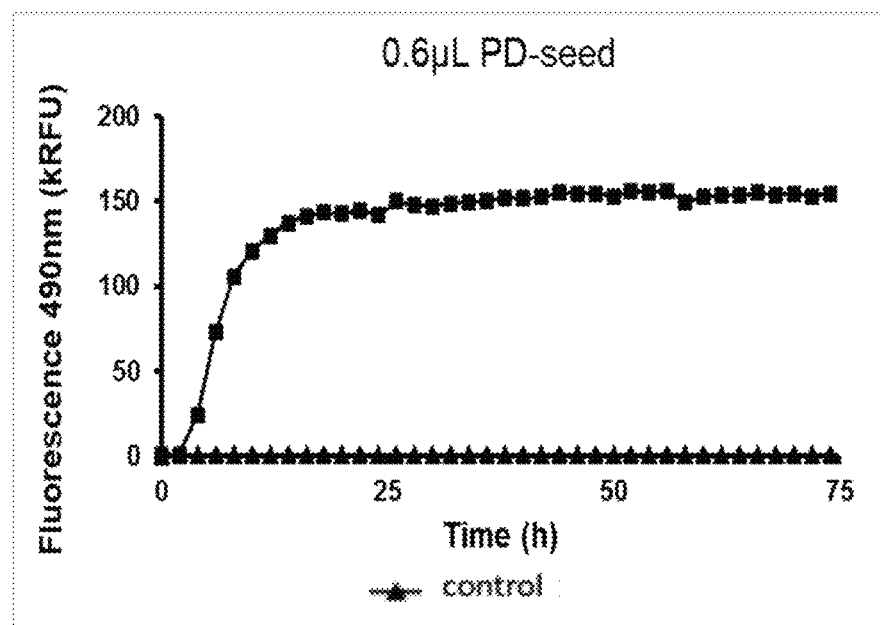
FIG. 12A shows an aggregation curve where the products (e.g., misfolded αS aggregates) of a first round of bead-assisted αS-PMCA on the CSF of a PD patient presenting pure PD pathology were used to seed a second round of αS-PMCA.
Figure 12B:
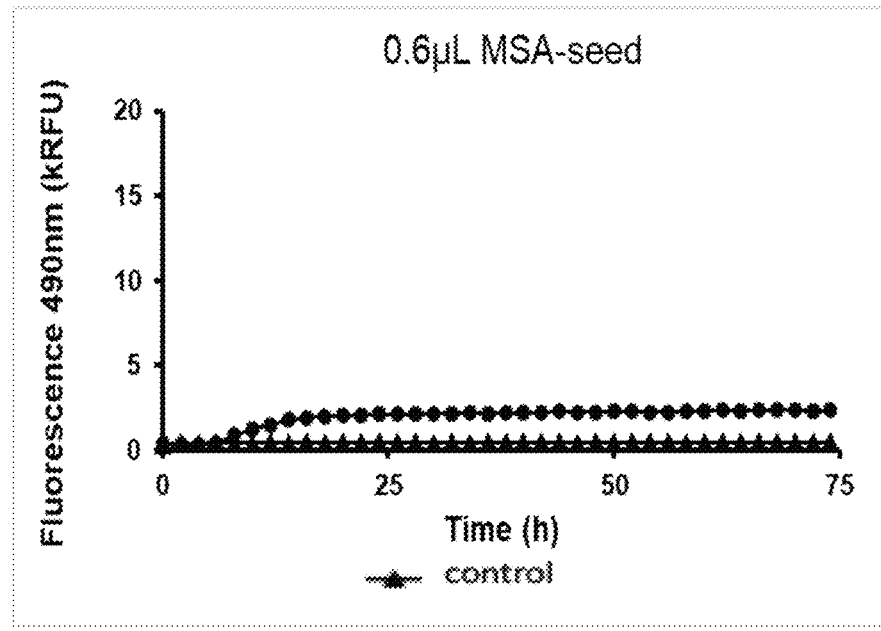
FIG. 12B shows an aggregation curve where the products of a first round of bead-assisted αS-PMCA on the CSF of an MSA patient presenting pure MSA pathology were used to seed a second round of αS-PMCA.

The qualitative differences in ThT fluorescence were maintained when the αS-PMCA reaction products (e.g., misfolded αS aggregates) amplified from PD or MSA CSF were replicated serially at the expense of monomeric αS substrate. For these studies, 0.6 µL of the products (e.g., misfolded αS aggregates) of a first round of bead-assisted αS-PMCA on the CSF of a PD or MSA patient presenting pure PD or MSA pathology were used to seed a second round of αS-PMCA. More specifically, the second round of αS-PMCA was performed exactly as in the previous example, except that 39.4 µL of CSF was used, plus 0.6 µL of the "seed," instead of 40 µL of CSF. For PD and MSA, the product maintained the relatively high fluorescence signal for PD and relatively low fluorescence for MSA (FIGS. 12A and 12B).

Figure 13A:
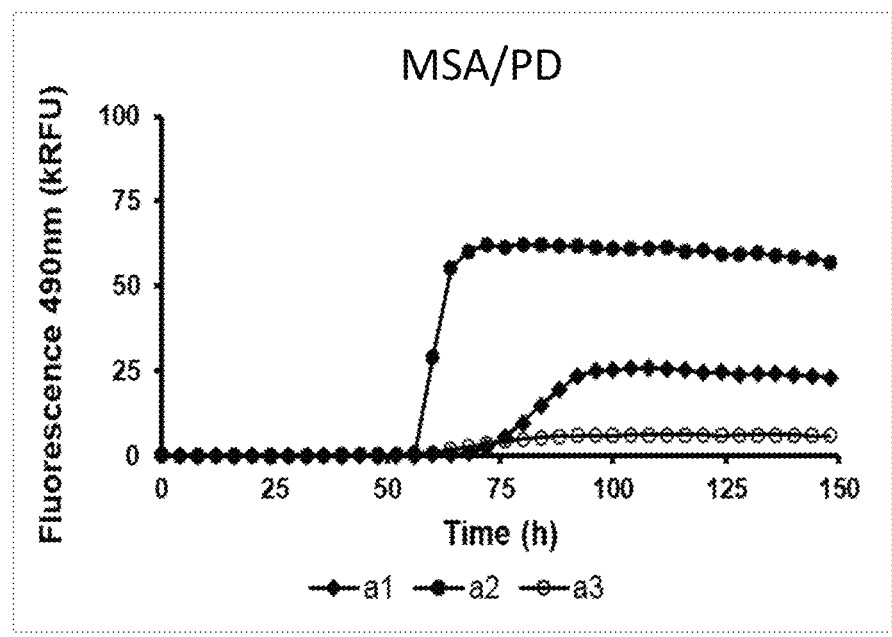
FIG. 13A shows an aggregation curve for αS-PMCA of an MSA patient's CSF where beads were included in the incubation mixture. The patient presents a mixture of PD and MSA pathologies. Indicators a1, a2, and a3 are the replicates of the same sample.
Figure 13B:
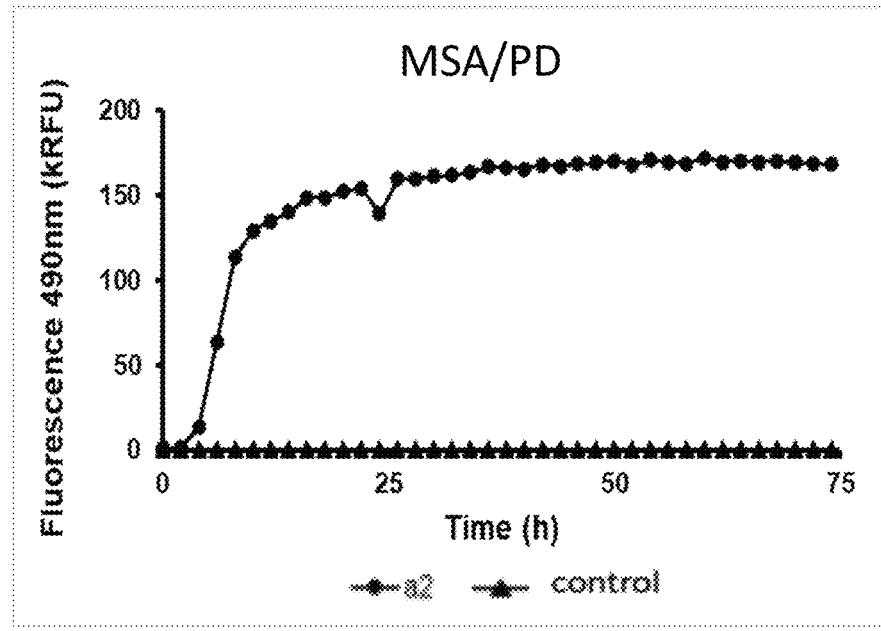
FIG. 13B shows an aggregation curve where the αS-PMCA products of replicate a2 from FIG. 13A were used to seed a second round of αS-PMCA.

3. αS-PMCA and Serial Amplification of an MSA Sample Presenting a Spectrum of Pathologies FIG. 13A shows an aggregation curve for αS-PMCA of an MSA patient's CSF where beads were included in the incubation mixture. The patient presents a mixture of PD and MSA pathologies. Indicators a1, a2, and a3 are the replicates of the same sample. The αS-PMCA products (e.g., misfolded αS aggregates) of replicate a2 (most-PD-like) from FIG. 13A were used to seed a second round of αS-PMCA. FIG. 13B shows the aggregation curve. These results suggest that this clinically diagnosed MSA patient has a mixture of PD and MSA pathology. This is consistent with previous reports that there is a spectrum of αS pathology. Thus, some patients present pure PD pathology (FIGS. 11A and 11B); some patients present pure MSA pathology (FIGS. 12A and 12B); and some patients have mixtures of both structures (FIGS. 13A and 13B).

Figure 14:
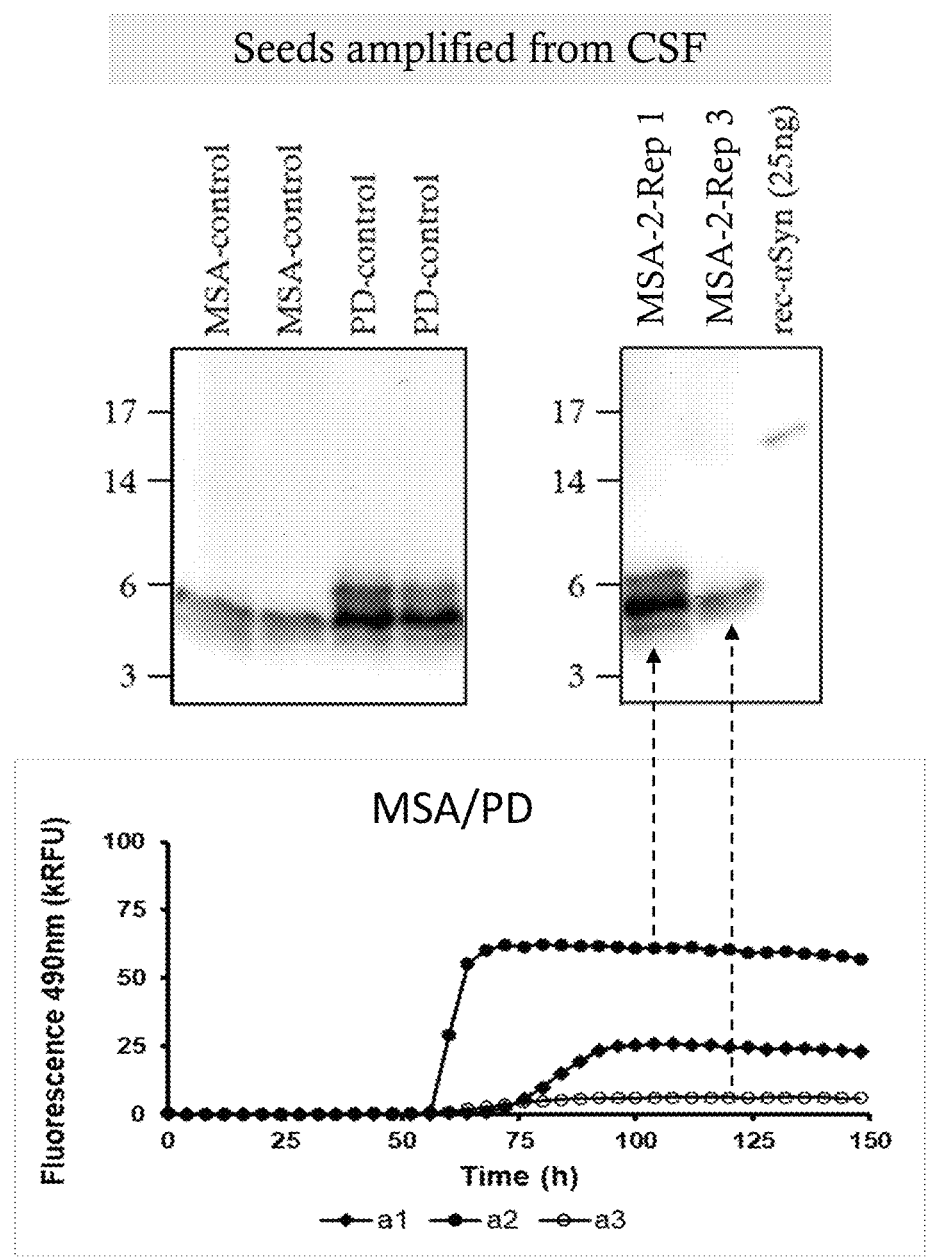
FIG. 14 shows the results of proteinase K digestion of the αS-PMCA products of replicates a2 and a3 from FIG. 13A.

4. PK Digestion of the αS-PMCA Products (e.g., Misfolded αS Aggregates) of Replicates a2 and a3 from FIG. 13A The αS-PMCA products of replicates a2 and a3 from FIG. 13A were evaluated with PK digestion. The results are shown in FIG. 14. The replicate with PD-like aggregation features (a2) shows an electrophoretic pattern observed in PD samples (PD-control). The replicate with MSA-like aggregation curve (a3) produced an electrophoretic pattern after PK digestion that is consistent with other MSA samples (MSA controls). Therefore, αS-PMCA using beads allows MSA and PD aggregates to faithfully replicate and maintain their features, generating synthetic aggregates that behave like endogenous seeds. Moreover, the fluorescence characteristics and the PK digestion pattern allow for the faithful replication to be used for diagnostic purposes.

Unless defined otherwise, all technical and scientific terms used herein have the same meaning as commonly understood by one of ordinary skill in the art to which this invention belongs.

Where a range of values is provided, each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

The term "about" in conjunction with a number is intended to include ±10% of the number. This is true whether "about" is modifying a stand-alone number or modifying a number at either or both ends of a range of numbers. In other words, "about 10" means from 9 to 11. Likewise, "about 10 to about 20" contemplates 9 to 22 and 11 to 18. In the absence of the term "about," the exact number is intended. In other words, "10" means 10.

The singular forms "a", "and", and "the" include plural referents unless the context clearly dictates otherwise. Thus, for example, reference to "a sample" also includes a plurality of such samples and reference to "a monomeric αS substrate" includes reference to one or more such molecule, and so forth.

The complete disclosure of all patents, patent applications, and publications, and electronically available material cited herein are incorporated by reference, whether or not the specific citation herein so states. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

---

What is claimed is:

1. A method for differentiating a diagnosis of Parkinson's Disease (PD) from a diagnosis of Multiple System Atrophy (MSA) in a human subject, the method comprising:
 (A) contacting a cerebrospinal fluid (CSF) or a brain homogenate (BH) sample (i) obtained from the human subject and (ii) comprising soluble, misfolded alpha-synuclein (αS) protein, with a pre-incubation mixture, the pre-incubation mixture comprising:
  (1) a monomeric αS substrate;
  (2) a buffer composition;
  (3) sodium chloride (NaCl); and
  (4) a fluorescent protein aggregation indicator,
 to form an incubation mixture;
 (B) incubating and agitating the incubation mixture to form an incubated mixture comprising misfolded αS aggregates;
 (C) illuminating the incubated mixture with a wavelength of light that excites the fluorescent protein aggregation indicator, including:
  (1) determining an initial average fluorescence ($AF_i$) of the incubated mixture prior to the formation of the misfolded αS aggregates;
  (2) determining a standard deviation ($SD_i$) of the $AF_i$; and
  (3) determining a maximum fluorescence (Fmax) of the incubated mixture after the formation of the misfolded αS aggregates; and
 (D) diagnosing the human subject as having PD or MSA, where:
  (1) if the Fmax is from about $22.2 \times SD_i + AF_i$ to $250 \times SD_i + AF_i$, the patient is diagnosed as having MSA; and
  (2) if the Fmax is above $250 \times SD_i + AF_i$, the patient is diagnosed as having PD.

2. The method of claim 1, further comprising contacting the misfolded αS aggregates with a protease after step D(2).

3. The method of claim 1, further comprising evaluating the structure of the misfolded αS aggregates using circular dichroism after step D(2).

4. The method of claim 1, further comprising evaluating the structure of the misfolded αS aggregates using cryo-electron tomography after step D(2).

5. The method of claim 1, wherein the monomeric αS substrate comprises SEQ ID NO: 2.

6. The method of claim 5, wherein the monomeric αS substrate is present in a concentration of about 1 mg/mL.

7. The method of claim 1, wherein the buffer composition comprises piperazine-N,N'-bis(2-ethanesulfonic acid) (PIPES).

8. The method of claim 1, wherein the buffer composition has a pH of about 6.5.

9. The method of claim 1, wherein the NaCl is present in a concentration of about 500 mM.

10. The method of claim 1, wherein the fluorescent protein aggregation indicator comprises thioflavin-T (ThT).

11. The method of claim 10, wherein the ThT is present in a concentration of about 5 μM.

12. The method of claim 1, further comprising contacting the misfolded αS aggregates with an oligothiophene after step D(2).

13. The method of claim 1, further comprising evaluating the structure of the misfolded αS aggregates using Fourier-transformed infrared spectroscopy after step D(2).

14. The method of claim 1, further comprising, after step D(2), contacting the misfolded αS aggregates to a cell and evaluating toxicity of the misfolded αS aggregates to the cell.

15. A method for differentiating a diagnosis of Parkinson's Disease (PD) from a diagnosis of Multiple System Atrophy (MSA) in a human subject, the method comprising:
 (A) contacting a cerebrospinal fluid (CSF) or a brain homogenate (BH) sample (i) obtained from the human subject and (ii) comprising soluble, misfolded alpha-synuclein (αS) protein, with a pre-incubation mixture, the pre-incubation mixture comprising:
  (1) a monomeric αS substrate;
  (2) a buffer composition;
  (3) sodium chloride (NaCl); and
  (4) a fluorescent protein aggregation indicator,
 to form an incubation mixture;
 (B) incubating and agitating the incubation mixture to form an incubated mixture comprising misfolded αS aggregates;
 (C) illuminating the incubated mixture with a wavelength of light that excites the fluorescent protein aggregation indicator, including determining a maximum fluorescence (Fmax) of the incubated mixture; and
 (D) diagnosing the human subject as having PD or MSA, where:
  (1) if the Fmax is from about 200 to about 1800 relative fluorescence units (RFU), the patient is diagnosed as having MSA; and
  (2) if the Fmax is above 2000 RFU, the patient is diagnosed as having PD.

16. The method of claim 15, further comprising contacting the misfolded αS aggregates with a protease after step D(2).

17. The method of claim 15, further comprising evaluating the structure of the misfolded αS aggregates using circular dichroism after step D(2).

18. The method of claim 15, further comprising evaluating the structure of the misfolded αS aggregates using cryo-electron tomography after step D(2).

19. The method of claim 15, wherein the monomeric αS substrate comprises-SEQ ID NO: 2.

20. The method of claim 19, wherein the monomeric αS substrate is present in a concentration of about 1 mg/mL.

21. The method of claim 15, wherein the buffer composition comprises piperazine-N,N'-bis(2-ethanesulfonic acid) (PIPES).

22. The method of claim 15, wherein the buffer composition has a pH of about 6.5.

23. The method of claim 15, wherein the NaCl is present in a concentration of about 500 mM.

24. The method of claim 15, wherein the fluorescent protein aggregation indicator comprises thioflavin-T (ThT).

25. The method of claim 24, wherein the ThT is present in a concentration of about 5 μM.

26. The method of claim 15, further comprising contacting the misfolded αS aggregates with an oligothiophene after step D(2).

27. The method of claim 15, further comprising evaluating the structure of the misfolded αS aggregates using Fourier-transformed infrared spectroscopy after step D(2).

28. The method of claim 15, further comprising, after step D(2), contacting the misfolded αS aggregates to a cell and evaluating toxicity of the misfolded αS aggregates to the cell.

29. A method for differential diagnosis of Parkinson's Disease (PD) from Multiple System Atrophy (MSA) in a human subject, the method comprising:
- (A) contacting a cerebrospinal fluid (CSF) or a brain homogenate (BH) sample (i) obtained from the human subject and (ii) comprising soluble, misfolded alpha-synuclein (αS) protein, with a pre-incubation mixture, the pre-incubation mixture comprising:
  - (1) a monomeric αS substrate;
  - (2) a buffer composition;
  - (3) sodium chloride (NaCl);
  - (4) a fluorescent protein aggregation indicator; and
  - (5) a bead comprising $Si_3N_4$ or borosilicate glass, to form an incubation mixture;
- (B) incubating and agitating the incubation mixture to form an incubated mixture comprising misfolded αS aggregates;
- (C) illuminating the incubated mixture with a wavelength of light that excites the fluorescent protein aggregation indicator, including:
  - (1) determining an average fluorescence ($AF_i$) of the incubated mixture prior to the formation of the misfolded αS aggregates;
  - (2) determining a standard deviation ($SD_i$) of the $AF_i$; and
  - (3) determining a maximum fluorescence (Fmax) of the incubated mixture after the formation of the misfolded αS aggregates; and
- (D) diagnosing the human subject as having PD or MSA, where:
  - (1) if the Fmax is from about $9.6 \times SD_i + AF_i$ to $180 \times SD_i + AF_i$, the patient is diagnosed as having MSA; and
  - (2) if the Fmax is above $180 \times SD_i + AF_i$, the patient is diagnosed as having PD.

30. The method of claim 29, wherein the bead is a $Si_3N_4$ bead having a diameter of from about 2.3 mm to about 5 mm.

31. The method of claim 29, further comprising contacting the misfolded αS aggregates with a protease after step D(2).

32. The method of claim 29, further comprising evaluating the structure of the misfolded αS aggregates using circular dichroism after step D(2).

33. The method of claim 29, further comprising evaluating the structure of the misfolded αS aggregates using cryo-electron tomography after step D(2).

34. The method of claim 29, wherein the monomeric αS substrate comprises SEQ ID NO: 2.

35. The method of claim 34, wherein the monomeric αS substrate is present in a concentration of about 0.3 mg/mL.

36. The method of claim 29, wherein the buffer composition comprises piperazine-N,N'-bis(2-ethanesulfonic acid) (PIPES).

37. The method of claim 29, wherein the buffer composition has a pH of about 6.5.

38. The method of claim 29, wherein the NaCl is present in a concentration of about 500 mM.

39. The method of claim 29, wherein the fluorescent protein aggregation indicator comprises thioflavin-T (ThT).

40. The method of claim 39, wherein the ThT is present in a concentration of less than or equal to about 10 μM.

41. The method of claim 29, further comprising contacting the misfolded αS aggregates with an oligothiophene after step D(2).

42. The method of claim 29, further comprising evaluating the structure of the misfolded αS aggregates using Fourier-transformed infrared spectroscopy after step D(2).

43. The method of claim 29, further comprising, after step D(2), contacting the misfolded αS aggregates to a cell and evaluating toxicity of the misfolded αS aggregates to the cell.

\* \* \* \* \*

SEQUENCE LISTING

```
<160> NUMBER OF SEQ ID NOS: 19

<210> SEQ ID NO 1
<211> LENGTH: 140
<212> TYPE: PRT
<213> ORGANISM: Artificial Sequence
<220> FEATURE:
<223> OTHER INFORMATION: Synthetic

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Thr Gly Phe Val Lys
            85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asn Glu Ala Tyr Glu Met Pro
            115                 120                 125

Ser Glu Glu Gly Tyr Gln Asp Tyr Glu Pro Glu Ala
        130                 135                 140

<210> SEQ ID NO 2
<211> LENGTH: 146
<212> TYPE: PRT
<213> ORGANISM: Artificial Sequence
<220> FEATURE:
<223> OTHER INFORMATION: Synthetic

<400> SEQUENCE: 2

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
```

```
                    20                  25                  30
Thr Lys Glu Gly Val Leu Tyr Val Gly Ser Lys Thr Lys Glu Gly Val
                35                  40                  45

Val His Gly Val Ala Thr Val Ala Glu Lys Thr Lys Glu Gln Val Thr
            50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Thr Gly Phe Val Lys
                85                  90                  95

Lys Asp Gln Leu Gly Lys Asn Glu Glu Gly Ala Pro Gln Glu Gly Ile
                100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala His His His His
            130                 135                 140

His His
145

<210> SEQ ID NO 3
<211> LENGTH: 146
<212> TYPE: PRT
<213> ORGANISM: Artificial Sequence
<220> FEATURE:
<223> OTHER INFORMATION: Synthetic

<400> SEQUENCE: 3

His His His His His His Met Asp Val Phe Met Lys Gly Leu Ser Lys
1               5                   10                  15

Ala Lys Glu Gly Val Val Ala Ala Ala Glu Lys Thr Lys Gln Gly Val
                20                  25                  30

Ala Glu Ala Ala Gly Lys Thr Lys Glu Gly Val Leu Tyr Val Gly Ser
            35                  40                  45

Lys Thr Lys Glu Gly Val Val His Gly Val Ala Thr Val Ala Glu Lys
50                  55                  60

Thr Lys Glu Gln Val Thr Asn Val Gly Gly Ala Val Val Thr Gly Val
65                  70                  75                  80

Thr Ala Val Ala Gln Lys Thr Val Glu Gly Ala Gly Ser Ile Ala Ala
                85                  90                  95

Ala Thr Gly Phe Val Lys Lys Asp Gln Leu Gly Lys Asn Glu Glu Gly
            100                 105                 110

Ala Pro Gln Glu Gly Ile Leu Glu Asp Met Pro Val Asp Pro Asp Asn
            115                 120                 125

Glu Ala Tyr Glu Met Pro Ser Glu Glu Gly Tyr Gln Asp Tyr Glu Pro
            130                 135                 140

Glu Ala
145

<210> SEQ ID NO 4
<211> LENGTH: 147
<212> TYPE: PRT
<213> ORGANISM: Artificial Sequence
<220> FEATURE:
<223> OTHER INFORMATION: Synthetic

<400> SEQUENCE: 4

Met Asp Val Phe Met Lys Gly Leu Ser Lys Ala Lys Glu Gly Val Val
1               5                   10                  15
```

```
Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
            35                  40                  45

Val His Gly Val Ala Thr Val Ala Glu Lys Thr Lys Glu Gln Val Thr
50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala Asp Tyr Lys Asp
            130                 135                 140

Asp Asp Asp
145
```

<210> SEQ ID NO 5
<211> LENGTH: 147
<212> TYPE: PRT
<213> ORGANISM: Artificial Sequence
<220> FEATURE:
<223> OTHER INFORMATION: Synthetic

<400> SEQUENCE: 5

```
Asp Tyr Lys Asp Asp Asp Met Asp Val Phe Met Lys Gly Leu Ser
1               5                   10                  15

Lys Ala Lys Glu Gly Val Val Ala Ala Ala Glu Lys Thr Lys Gln Gly
            20                  25                  30

Val Ala Glu Ala Ala Gly Lys Thr Lys Glu Gly Val Leu Tyr Val Gly
            35                  40                  45

Ser Lys Thr Lys Glu Gly Val Val His Gly Val Ala Thr Val Ala Glu
50                  55                  60

Lys Thr Lys Glu Gln Val Thr Asn Val Gly Gly Ala Val Val Thr Gly
65                  70                  75                  80

Val Thr Ala Val Ala Gln Lys Thr Val Glu Gly Ala Gly Ser Ile Ala
                85                  90                  95

Ala Ala Thr Gly Phe Val Lys Lys Asp Gln Leu Gly Lys Asn Glu Glu
            100                 105                 110

Gly Ala Pro Gln Glu Gly Ile Leu Glu Asp Met Pro Val Asp Pro Asp
            115                 120                 125

Asn Glu Ala Tyr Glu Met Pro Ser Glu Glu Gly Tyr Gln Asp Tyr Glu
            130                 135                 140

Pro Glu Ala
145
```

<210> SEQ ID NO 6
<211> LENGTH: 148
<212> TYPE: PRT
<213> ORGANISM: Artificial Sequence
<220> FEATURE:
<223> OTHER INFORMATION: Synthetic

<400> SEQUENCE: 6

```
Met Asp Val Phe Met Lys Gly Leu Ser Lys Ala Lys Glu Gly Val Val
1               5                   10                  15
```

Ala Ala Ala Glu Lys Thr Lys Gln Gly Val Ala Glu Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala Asp Tyr Lys Asp
    130                 135                 140

Asp Asp Asp Lys
145

<210> SEQ ID NO 7
<211> LENGTH: 148
<212> TYPE: PRT
<213> ORGANISM: Artificial Sequence
<220> FEATURE:
<223> OTHER INFORMATION: Synthetic

<400> SEQUENCE: 7

Asp Tyr Lys Asp Asp Asp Lys Met Asp Val Phe Met Lys Gly Leu
1               5                   10                  15

Ser Lys Ala Lys Glu Gly Val Val Ala Ala Glu Lys Thr Lys Gln
            20                  25                  30

Gly Val Ala Glu Ala Ala Gly Lys Thr Lys Glu Gly Val Leu Tyr Val
        35                  40                  45

Gly Ser Lys Thr Lys Glu Gly Val Val His Gly Val Ala Thr Val Ala
    50                  55                  60

Glu Lys Thr Lys Glu Gln Val Thr Asn Val Gly Gly Ala Val Val Thr
65                  70                  75                  80

Gly Val Thr Ala Val Ala Gln Lys Thr Val Glu Gly Ala Gly Ser Ile
                85                  90                  95

Ala Ala Ala Thr Gly Phe Val Lys Lys Asp Gln Leu Gly Lys Asn Glu
            100                 105                 110

Glu Gly Ala Pro Gln Glu Gly Ile Leu Glu Asp Met Pro Val Asp Pro
        115                 120                 125

Asp Asn Glu Ala Tyr Glu Met Pro Ser Glu Glu Gly Tyr Gln Asp Tyr
    130                 135                 140

Glu Pro Glu Ala
145

<210> SEQ ID NO 8
<211> LENGTH: 147
<212> TYPE: PRT
<213> ORGANISM: Artificial Sequence
<220> FEATURE:
<223> OTHER INFORMATION: Synthetic

<400> SEQUENCE: 8

Met Asp Val Phe Met Lys Gly Leu Ser Lys Ala Lys Glu Gly Val Val

```
                1               5                  10                 15
            Ala Ala Ala Glu Lys Thr Lys Gln Gly Val Ala Glu Ala Ala Gly Lys
                         20                  25                 30

Thr Lys Glu Gly Val Leu Tyr Val Gly Ser Lys Thr Lys Glu Gly Val
                         35                  40                 45

Val His Gly Val Ala Thr Val Ala Glu Lys Thr Lys Glu Gln Val Thr
                 50                  55                 60

Asn Val Gly Gly Ala Val Val Thr Gly Val Thr Ala Val Ala Gln Lys
             65                  70                  75                 80

Thr Val Glu Gly Ala Gly Ser Ile Ala Ala Ala Thr Gly Phe Val Lys
                         85                  90                 95

Lys Asp Gln Leu Gly Lys Asn Glu Glu Gly Ala Pro Gln Glu Gly Ile
                         100                 105                110

Leu Glu Asp Met Pro Val Asp Pro Asp Asn Glu Ala Tyr Glu Met Pro
                         115                 120                125

Ser Glu Glu Gly Tyr Gln Asp Tyr Glu Pro Glu Ala Asp Tyr Lys Asp
                         130                 135                140

Asp Asp Lys
            145

<210> SEQ ID NO 9
<211> LENGTH: 147
<212> TYPE: PRT
<213> ORGANISM: Artificial Sequence
<220> FEATURE:
<223> OTHER INFORMATION: Synthetic

<400> SEQUENCE: 9

Asp Tyr Lys Asp Asp Asp Lys Met Asp Val Phe Met Lys Gly Leu Ser
            1               5                  10                 15

Lys Ala Lys Glu Gly Val Val Ala Ala Ala Glu Lys Thr Lys Gln Gly
                         20                  25                 30

Val Ala Glu Ala Ala Gly Lys Thr Lys Glu Gly Val Leu Tyr Val Gly
                         35                  40                 45

Ser Lys Thr Lys Glu Gly Val Val His Gly Val Ala Thr Val Ala Glu
                 50                  55                 60

Lys Thr Lys Glu Gln Val Thr Asn Val Gly Gly Ala Val Val Thr Gly
             65                  70                  75                 80

Val Thr Ala Val Ala Gln Lys Thr Val Glu Gly Ala Gly Ser Ile Ala
                         85                  90                 95

Ala Ala Thr Gly Phe Val Lys Lys Asp Gln Leu Gly Lys Asn Glu Glu
                         100                 105                110

Gly Ala Pro Gln Glu Gly Ile Leu Glu Asp Met Pro Val Asp Pro Asp
                         115                 120                125

Asn Glu Ala Tyr Glu Met Pro Ser Glu Glu Gly Tyr Gln Asp Tyr Glu
                         130                 135                140

Pro Glu Ala
            145

<210> SEQ ID NO 10
<211> LENGTH: 149
<212> TYPE: PRT
<213> ORGANISM: Artificial Sequence
<220> FEATURE:
<223> OTHER INFORMATION: Synthetic

<400> SEQUENCE: 10
```

```
Met Asp Val Phe Met Lys Gly Leu Ser Lys Ala Lys Glu Gly Val
1               5                   10                  15

Ala Ala Ala Glu Lys Thr Lys Gln Gly Val Ala Glu Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala Tyr Pro Tyr Asp
            130                 135                 140

Val Pro Asp Tyr Ala
145

<210> SEQ ID NO 11
<211> LENGTH: 149
<212> TYPE: PRT
<213> ORGANISM: Artificial Sequence
<220> FEATURE:
<223> OTHER INFORMATION: Synthetic

<400> SEQUENCE: 11

Tyr Pro Tyr Asp Val Pro Asp Tyr Ala Met Asp Val Phe Met Lys Gly
1               5                   10                  15

Leu Ser Lys Ala Lys Glu Gly Val Val Ala Ala Ala Glu Lys Thr Lys
            20                  25                  30

Gln Gly Val Ala Glu Ala Ala Gly Lys Thr Lys Glu Gly Val Leu Tyr
            35                  40                  45

Val Gly Ser Lys Thr Lys Glu Gly Val Val His Gly Val Ala Thr Val
50                  55                  60

Ala Glu Lys Thr Lys Glu Gln Val Thr Asn Val Gly Gly Ala Val Val
65                  70                  75                  80

Thr Gly Val Thr Ala Val Ala Gln Lys Thr Val Glu Gly Ala Gly Ser
                85                  90                  95

Ile Ala Ala Ala Thr Gly Phe Val Lys Lys Asp Gln Leu Gly Lys Asn
            100                 105                 110

Glu Glu Gly Ala Pro Gln Glu Gly Ile Leu Glu Asp Met Pro Val Asp
            115                 120                 125

Pro Asp Asn Glu Ala Tyr Glu Met Pro Ser Glu Glu Gly Tyr Gln Asp
            130                 135                 140

Tyr Glu Pro Glu Ala
145

<210> SEQ ID NO 12
<211> LENGTH: 149
<212> TYPE: PRT
<213> ORGANISM: Artificial Sequence
<220> FEATURE:
<223> OTHER INFORMATION: Synthetic

<400> SEQUENCE: 12
```

```
Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
            35                  40                  45

Val His Gly Val Ala Thr Val Ala Glu Lys Thr Lys Glu Gln Val Thr
        50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
                100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala Tyr Ala Tyr Asp
            130                 135                 140

Val Pro Asp Tyr Ala
145

<210> SEQ ID NO 13
<211> LENGTH: 149
<212> TYPE: PRT
<213> ORGANISM: Artificial Sequence
<220> FEATURE:
<223> OTHER INFORMATION: Synthetic

<400> SEQUENCE: 13

Tyr Ala Tyr Asp Val Pro Asp Tyr Ala Met Asp Val Phe Met Lys Gly
1               5                   10                  15

Leu Ser Lys Ala Lys Glu Gly Val Val Ala Ala Ala Glu Lys Thr Lys
            20                  25                  30

Gln Gly Val Ala Glu Ala Ala Gly Lys Thr Lys Glu Gly Val Leu Tyr
            35                  40                  45

Val Gly Ser Lys Thr Lys Glu Gly Val Val His Gly Val Ala Thr Val
    50                  55                  60

Ala Glu Lys Thr Lys Glu Gln Val Thr Asn Val Gly Gly Ala Val Val
65                  70                  75                  80

Thr Gly Val Thr Ala Val Ala Gln Lys Thr Val Glu Gly Ala Gly Ser
                85                  90                  95

Ile Ala Ala Ala Thr Gly Phe Val Lys Lys Asp Gln Leu Gly Lys Asn
                100                 105                 110

Glu Glu Gly Ala Pro Gln Glu Gly Ile Leu Glu Asp Met Pro Val Asp
            115                 120                 125

Pro Asp Asn Glu Ala Tyr Glu Met Pro Ser Glu Glu Gly Tyr Gln Asp
            130                 135                 140

Tyr Glu Pro Glu Ala
145

<210> SEQ ID NO 14
<211> LENGTH: 149
<212> TYPE: PRT
<213> ORGANISM: Artificial Sequence
<220> FEATURE:
<223> OTHER INFORMATION: Synthetic
```

```
<400> SEQUENCE: 14

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala Tyr Asp Val Pro
    130                 135                 140

Asp Tyr Ala Ser Leu
145

<210> SEQ ID NO 15
<211> LENGTH: 149
<212> TYPE: PRT
<213> ORGANISM: Artificial Sequence
<220> FEATURE:
<223> OTHER INFORMATION: Synthetic

<400> SEQUENCE: 15

Tyr Asp Val Pro Asp Tyr Ala Ser Leu Met Asp Val Phe Met Lys Gly
1               5                   10                  15

Leu Ser Lys Ala Lys Glu Gly Val Val Ala Ala Ala Glu Lys Thr Lys
            20                  25                  30

Gln Gly Val Ala Glu Ala Ala Gly Lys Thr Lys Glu Gly Val Leu Tyr
        35                  40                  45

Val Gly Ser Lys Thr Lys Glu Gly Val Val His Gly Val Ala Thr Val
    50                  55                  60

Ala Glu Lys Thr Lys Glu Gln Val Thr Asn Val Gly Gly Ala Val Val
65                  70                  75                  80

Thr Gly Val Thr Ala Val Ala Gln Lys Thr Val Glu Gly Ala Gly Ser
                85                  90                  95

Ile Ala Ala Ala Thr Gly Phe Val Lys Lys Asp Gln Leu Gly Lys Asn
            100                 105                 110

Glu Glu Gly Ala Pro Gln Glu Gly Ile Leu Glu Asp Met Pro Val Asp
        115                 120                 125

Pro Asp Asn Glu Ala Tyr Glu Met Pro Ser Glu Glu Gly Tyr Gln Asp
    130                 135                 140

Tyr Glu Pro Glu Ala
145

<210> SEQ ID NO 16
<211> LENGTH: 150
<212> TYPE: PRT
<213> ORGANISM: Artificial Sequence
<220> FEATURE:
<223> OTHER INFORMATION: Synthetic
```

<400> SEQUENCE: 16

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Gly Lys
            20                  25                  30

Thr Lys Glu Gly Val Leu Tyr Val Gly Ser Lys Thr Lys Glu Gly Val
            35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Thr Gly Phe Val Lys
            85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala Glu Gln Lys Leu
130                 135                 140

Ile Ser Glu Glu Asp Leu
145                 150

<210> SEQ ID NO 17
<211> LENGTH: 150
<212> TYPE: PRT
<213> ORGANISM: Artificial Sequence
<220> FEATURE:
<223> OTHER INFORMATION: Synthetic

<400> SEQUENCE: 17

Glu Gln Lys Leu Ile Ser Glu Glu Asp Leu Met Asp Val Phe Met Lys
1               5                   10                  15

Gly Leu Ser Lys Ala Lys Glu Gly Val Val Ala Ala Ala Glu Lys Thr
            20                  25                  30

Lys Gln Gly Val Ala Glu Ala Ala Gly Lys Thr Lys Glu Gly Val Leu
            35                  40                  45

Tyr Val Gly Ser Lys Thr Lys Glu Gly Val Val His Gly Val Ala Thr
    50                  55                  60

Val Ala Glu Lys Thr Lys Glu Gln Val Thr Asn Val Gly Gly Ala Val
65                  70                  75                  80

Val Thr Gly Val Thr Ala Val Ala Gln Lys Thr Val Glu Gly Ala Gly
            85                  90                  95

Ser Ile Ala Ala Ala Thr Gly Phe Val Lys Lys Asp Gln Leu Gly Lys
            100                 105                 110

Asn Glu Glu Gly Ala Pro Gln Glu Gly Ile Leu Glu Asp Met Pro Val
            115                 120                 125

Asp Pro Asp Asn Glu Ala Tyr Glu Met Pro Ser Glu Glu Gly Tyr Gln
130                 135                 140

Asp Tyr Glu Pro Glu Ala
145                 150

<210> SEQ ID NO 18
<211> LENGTH: 154
<212> TYPE: PRT
<213> ORGANISM: Artificial Sequence
<220> FEATURE:

<223> OTHER INFORMATION: Synthetic

<400> SEQUENCE: 18

```
Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala Gly Lys Pro Ile
            130                 135                 140

Pro Asn Pro Leu Leu Gly Leu Asp Ser Thr
145                 150
```

<210> SEQ ID NO 19
<211> LENGTH: 154
<212> TYPE: PRT
<213> ORGANISM: Artificial Sequence
<220> FEATURE:
<223> OTHER INFORMATION: Synthetic

<400> SEQUENCE: 19

```
Gly Lys Pro Ile Pro Asn Pro Leu Leu Gly Leu Asp Ser Thr Met Asp
1               5                   10                  15

Val Phe Met Lys Gly Leu Ser Lys Ala Lys Glu Gly Val Val Ala Ala
            20                  25                  30

Ala Glu Lys Thr Lys Gln Gly Val Ala Glu Ala Ala Gly Lys Thr Lys
        35                  40                  45

Glu Gly Val Leu Tyr Val Gly Ser Lys Thr Lys Glu Gly Val Val His
    50                  55                  60

Gly Val Ala Thr Val Ala Glu Lys Thr Lys Glu Gln Val Thr Asn Val
65                  70                  75                  80

Gly Gly Ala Val Val Thr Gly Val Thr Ala Val Ala Gln Lys Thr Val
                85                  90                  95

Glu Gly Ala Gly Ser Ile Ala Ala Ala Thr Gly Phe Val Lys Lys Asp
            100                 105                 110

Gln Leu Gly Lys Asn Glu Glu Gly Ala Pro Gln Glu Gly Ile Leu Glu
            115                 120                 125

Asp Met Pro Val Asp Pro Asp Asn Glu Ala Tyr Glu Met Pro Ser Glu
            130                 135                 140

Glu Gly Tyr Gln Asp Tyr Glu Pro Glu Ala
145                 150
```